(12) United States Patent
Pugh et al.

(10) Patent No.: US 11,202,726 B2
(45) Date of Patent: Dec. 21, 2021

(54) CONNECTORS AND ENCASEMENT FOR PERSONAL HYGIENE PRODUCT WITH A DIGITAL ELEMENT

(71) Applicant: Johnson & Johnson Consumer Inc., Skillman, NJ (US)

(72) Inventors: Randall B. Pugh, St. Johns, FL (US); Adam Toner, Jacksonville, FL (US); Jose Francisco Cau, San Jose dos Campos/SP (BR); DAvid Kimball, Flemington, NJ (US); William Chester Neeley, Melbourne, FL (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 579 days.

(21) Appl. No.: 16/130,403

(22) Filed: Sep. 13, 2018

(65) Prior Publication Data
US 2019/0105210 A1    Apr. 11, 2019

Related U.S. Application Data

(60) Provisional application No. 62/569,744, filed on Oct. 9, 2017.

(51) Int. Cl.
*A61F 13/20* (2006.01)
*A61B 5/20* (2006.01)
(Continued)

(52) U.S. Cl.
CPC .............. *A61F 13/84* (2013.01); *A61B 5/24* (2021.01); *A61B 5/291* (2021.01); *A61B 5/375* (2021.01); *A61B 5/4337* (2013.01); *A61B 5/6808* (2013.01); *A61F 13/42* (2013.01); *A61F 13/472* (2013.01); *A61F 13/49* (2013.01); *G08B 21/182* (2013.01); *G08B 21/20* (2013.01);
(Continued)

(58) Field of Classification Search
CPC ...... A61F 13/20; A61F 13/202; A61F 13/204; A61F 13/42; A61F 13/472; A61F 13/49; A61F 13/84; A61F 2013/424; A61F 2013/427; A61F 2013/8479; A61B 5/6808
See application file for complete search history.

(56) References Cited

U.S. PATENT DOCUMENTS

| | | | | |
|---|---|---|---|---|
| 5,868,723 A | * | 2/1999 | Al-Sabah | A61F 13/42 604/361 |
| 6,091,336 A | * | 7/2000 | Zand | A61F 13/42 137/123 |

(Continued)

FOREIGN PATENT DOCUMENTS

| | | |
|---|---|---|
| CN | 2860445 Y | 1/2007 |
| CN | 202154798 U | 3/2012 |

(Continued)

OTHER PUBLICATIONS

European Search Report for related EPA No. 18199119.1 dated Feb. 28, 2019.

*Primary Examiner* — Catharine L Anderson

(57) ABSTRACT

A personal hygiene product with a digital element is described. In one embodiment, a conductive sensor assembly is disposed within the personal hygiene product that includes one or more moisture sensors that generate a resistive and/or capacitive signal indicative of saturation of the personal hygiene product when in wetting contact with menstrual fluid.

16 Claims, 17 Drawing Sheets

(51) Int. Cl.
*A61F 13/84* (2006.01)
*A61F 13/49* (2006.01)
*A61F 13/42* (2006.01)
*A61F 13/472* (2006.01)
*G08B 21/24* (2006.01)
*A61B 5/00* (2006.01)
*G08B 25/10* (2006.01)
*G08B 21/20* (2006.01)
*G08B 21/18* (2006.01)
*A61B 5/24* (2021.01)
*A61B 5/291* (2021.01)
*A61B 5/375* (2021.01)
*A61B 10/00* (2006.01)
*A61B 5/15* (2006.01)

(52) U.S. Cl.
CPC ........... *G08B 21/245* (2013.01); *G08B 25/10* (2013.01); *A61B 5/1405* (2013.01); *A61B 5/150045* (2013.01); *A61B 5/150969* (2013.01); *A61B 2010/0074* (2013.01); *A61B 2505/07* (2013.01); *A61B 2562/029* (2013.01); *A61F 2013/421* (2013.01); *A61F 2013/424* (2013.01); *A61F 2013/427* (2013.01); *A61F 2013/8479* (2013.01)

(56) References Cited

U.S. PATENT DOCUMENTS

| | | | |
|---|---|---|---|
| 7,250,547 | B1 | 7/2007 | Hofmeister |
| 7,352,286 | B2* | 4/2008 | Chan ...................... A61F 13/42 |
| | | | 340/603 |
| 7,806,882 | B1* | 10/2010 | Larkin ................ A61F 13/2051 |
| | | | 604/385.18 |
| 10,117,790 | B2* | 11/2018 | Pugh ....................... A61F 13/84 |
| 10,702,423 | B1* | 7/2020 | Krasnow ................ A61F 13/42 |
| 10,905,371 | B2* | 2/2021 | Brief ...................... A61B 5/002 |
| 2011/0319845 | A1 | 12/2011 | Kuo et al. |
| 2012/0040655 | A1 | 2/2012 | Larkin |
| 2014/0296808 | A1 | 10/2014 | Curran |
| 2016/0045378 | A1* | 2/2016 | Geloen ....................... A61F 5/48 |
| | | | 604/361 |
| 2016/0250081 | A1* | 9/2016 | Pugh .................. A61F 13/2051 |
| | | | 604/361 |
| 2017/0340254 | A1* | 11/2017 | Davis ................ A61B 5/02042 |

FOREIGN PATENT DOCUMENTS

| | | |
|---|---|---|
| CN | 105326607 A | 2/2016 |
| EP | 3061433 A1 | 8/2016 |
| JP | 2005270599 A | 10/2005 |

* cited by examiner

CONNECTORS AND ENCASEMENT FOR PERSONAL HYGIENE PRODUCT WITH A DIGITAL ELEMENT

CROSS-REFERENCE TO RELATED APPLICATIONS

This patent application claims the benefit of U.S. Provisional Application No. 62/569,744 filed Oct. 9, 2017.

BACKGROUND OF THE INVENTION

1. Field of the Invention

The present invention relates to personal hygiene products used for personal care, primarily for absorption or containment of bodily fluid, and more particularly, to a personal hygiene product with a digital element that may be utilized to sense and wirelessly communicate discharge related data to the user via a smart hand-held electronic device.

2. Discussion of the Related Art

The basic structure of a personal hygiene product has not varied greatly over time. The needs of users have also not varied; namely, to prevent seepage onto the skin, clothing, or external environment through maximized absorption and predictability of the personal hygiene product's absorption capacity. Personal hygiene products include tampons, bed pads, disposable adult diapers, disposable adult briefs, disposable sanitary napkins, sanitary napkins with adhesive strips and wings, and panty liners. Most people will at some point in their life use a personal hygiene product for some time. Personal hygiene products historically involve a one-size-fits-all approach.

A woman, for example, will use an estimated average of ten thousand (10,000) personal hygiene products in a lifetime. Even though feminine hygiene products come in different sizes and shapes designed for varying absorbent capacity, no product is one hundred (100) percent effective in preventing spills or leakage because variance in menstruation may lead to oversaturation. Each woman's menstrual flow varies over the course of her menstruation, with some days being lighter or heavier than others. Because of menstrual variance, accidents or overflows may occur where the personal hygiene product becomes oversaturated and spills outside of the absorbent area. Continued use of an oversaturated hygiene product may potentially lead to negative health impacts such as bacterial infections or toxic shock syndrome.

Many women manually track or monitor their menstrual cycle for predictability to avoid the unexpected start of menstruation in the absence of a personal hygiene product or accidents of the sort discussed above. There are over two hundred (200) smart device applications available to monitor menstruation manually. Users enter data into the application on a smart device, for example, a smart phone or other hand-held device, and the application generates data predicting, for example, menstrual start day, flow pattern, and length of menstruation. Many of these smart device applications issue alerts when menstruation is expected to start and end. All available devices; however, rely on data based on the subjective and manual entry of the user and may not reliably meet the primary needs most female hygiene product users have; namely, predictability and reliability. None of these applications can actively monitor the active absorption capacity of a personal hygiene product while an individual is wearing or using it.

Personal hygiene products are also used, for example, by the elderly, injured, persons with disability, and persons with incontinence. Personal hygiene products may be used in a variety of settings, for example, community, home, hospital, and nursing homes. In particular, hospitals and nursing home staff have limited resources to constantly monitor patients or residents who wear a personal hygiene product. The result is that patients and residents risk prolonged wear of a personal hygiene product that may result in sores or infection. Additionally, most hospitals and nursing homes are equipped with a lift team or machine to facilitate changing a personal hygiene product for a person who is not mobile. However, there may only be one lift team or machine per facility. As a result, a staff person changing a personal hygiene product alone risks injury on the job. The nursing and personal caretaker professions have the highest rates of injury resulting from on-the-job lifting because of individually lifting and maneuvering a patient's or resident's body to change a personal hygiene product during periodic checks during their shift.

Current efforts to monitor personal hygiene products in the settings above rely on periodic check and patient report. There is a need for hospitals and nursing homes to have real-time data and information to more efficiently respond to, for example, a personal hygiene product change, with adequate resources. Such a response will reduce injury occurrence and increase health safety for both the patient/resident and staff.

In addition to the need for predictability and reliability in the use of a personal hygiene product, a personal hygiene product is situated either proximate to or inserted into the body and as a result can collect data about patterns of discharge and biometrics in a way that a manual-entry application is unable to capture. This data is beneficial, to avoid social embarrassment, and for a user's overall health, for example, to provide accurate data to a physician or to alert the user if there are disruptions in normal patterns of bodily fluid discharge.

For example, menstrual issues and patterns of discharge are one of the most common reasons for a woman to see a doctor. Generally, a doctor's first response will be for the woman to keep a "menstrual diary" as a record of the period dates, length of periods, flow, and the like. Menstruation that departs from a normal monthly cycle, such as lasting longer or shorter than usual or not occurring at all, may indicate an underlying health issue. For example, abnormally long menstrual bleeding may indicate irregularities such as polyps, fibroids, cancer or infection within the uterus or cervix. A number of conditions may be revealed from menstrual flow data, including dysmenorrhea (painful periods), oligomenorrhoea (irregular periods), amenorrhea (lack of periods), and menorrhagia (heavy periods).

The location of a personal hygiene product may enable it to gather internal and external biometric data such as temperature or pH. Menstruation, for example, also includes discharge with biometric information. Monthly menstruation involves a process in which the uterus sheds the endometrium to allow a new lining to replace it. Menstrual fluid comprises uterine blood, meaning the endometrial tissue, vaginal secretions, and cervical fluids. Menstrual fluid also includes information on hormones such as estrogen and progesterone and enzymes related to pregnancy such as hydrolytic enzymes and lysosomes.

In the home health setting, for example, individuals receive periodic check-ups by home health staff ranging from multiple times daily to weekly. Isolated visits may not capture or accurately give warning if an individual has additional health issues if those issues do not present during a check-up. The valuable biometrics that may be gleamed from a personal hygiene product would accurately convey extensive data that if available electronically to a health care professional would provide a more accurate and holistic understanding of the patient's health. Additionally, a personal hygiene product with a digital element may facilitate remote monitoring either by a health care professional or family member.

The proper combination of a personal hygiene product incorporated with a digital element capable of interfacing with a smart hand-held electronic device would meet the ultimate needs of personal hygiene product consumers. The digital element needs to be biocompatible and comprise an array capable of wireless communication. Accordingly, there exists a need for providing a personal hygiene product capable of gathering, processing, and communicating data about the product's absorbent capacity and individual user's bodily fluid discharge to the smart hand-held electronic device of a user. There are also exists a need for an individual user to be able to interface with the data once communicated to the smart hand-held electronic device.

Existing connectors and enclosures or encasements are unable to fully meet the myriad requirements for a personal hygiene product incorporated with a digital element. One constraint is on the size of the enclosure and hence the connector. The enclosure should preferably be discrete and comfortable to be worn on the body. Another constraint is on cost, not only the disposable sensors but also the reusable signal acquisition device must be cost-competitive with established feminine hygiene systems. It is also very important for consumer acceptance that the system be easy to use. Existing connectors and enclosures suitable for consumer electronics may be intimidating to some potential customers. In addition, both the case and enclosure must also support a degree of water resistance.

Accordingly, the need exists for novel connector and enclosure designs for electrically functional personal hygiene systems.

SUMMARY OF THE INVENTION

A personal hygiene product with a digital element in accordance with the present invention overcomes the limitations with the prior art as briefly discussed above.

The present invention is directed to a device comprising a personal hygiene product with a digital element. In some embodiments, the personal hygiene product with a digital element comprises a digital element located on the exterior of a personal hygiene product that comes into direct contact with body fluid. In some embodiments, the personal hygiene product with a digital element comprises a digital element that is embedded within the absorbent core of a personal hygiene product. In some embodiments, the personal hygiene product with a digital element comprises a personal hygiene product with digital capabilities that connects to an external digital element.

In some embodiments, the personal hygiene product may be a feminine hygiene product used for menstruation or discharges of other bodily fluids. In some embodiments, the hygiene product may be a diaper, pad, or material used by adults to absorb or contain the discharge of bodily fluids.

In some embodiments, a conductive sensor assembly is disposed within a core of the personal hygiene product. The conductive sensor assembly may include a sensor array including one or more moisture sensors. Each moisture sensor may include a moisture sensitive switch coupled to a resistor where the resistance value of the moisture sensitive switch is less than the resistance value of the resistor.

In some embodiments, the digital element of the personal hygiene product may comprise a sensor array within the absorbent core of the hygiene product that magnetically connects to an external digital element. The digital element may comprise a battery, communication circuit, and sensor array.

In accordance with one aspect, the digital element may comprise a circuit board and battery power source.

In some embodiments, the digital element located on or within the personal hygiene product may comprise a sensor array and electrical components disposed on a substrate encapsulated by a biocompatible material. In some embodiments, the digital element may be printed onto the personal hygiene product and comprise a sensor array and electrical components located on a substrate.

In some embodiments, the digital element located on or within the personal hygiene device may comprise a sensor array, electrical components, and wireless communication device located on a substrate encapsulated by a biocompatible material.

In some embodiments, the sensor array may send data or information to the wireless communication device via a processor in the electrical components.

In some embodiments, the wireless communication device may communicate with a smart hand-held electronic device.

The digital element may be integrated into or embedded within the hygiene product and generate output information through a communication system with the ability to interface with a smart hand-held electronic device.

A person may use one hygiene product with a digital element that communicates wirelessly with a smart hand-held electronic device. A person may also use two hygiene products simultaneously where the digital element in one hygiene product communicates with a communication system in a second hygiene product that communicates with a smart hand-held electronic device. The digital element may be activated by some physical step, for example, connecting the conductive ribbon to the external digital element, unfolding a pad or pushing a tampon through the applicator.

In accordance with some embodiments, the digital element may comprise a sensor system including a sensor array to detect fluid levels in the product. The sensor system may also include a system controller configured to sample each sensor array to calculate liquid levels and provide an output control signal, and at least one actuator configured to receive the output control signal.

In accordance with one aspect, the digital element may comprise a sensor system including a transverse or longitudinal pair of sensors to detect fluid levels in the product. The sensor system may also include a system controller configured to sample each sensor array to calculate liquid levels and provide an output control signal, and at least one actuator configured to receive the output control signal.

In accordance with another aspect, the digital element may comprise a sensor system including a sensor array capable of detecting biometrics, for example, pH level and temperature, and provide an output control signal, and at least one actuator configured to receive the output control signal.

In accordance with another aspect, the digital element may comprise a sensor system including a sensor array capable of detecting biometrics, for example, hormonal levels, and provide an output control signal, and at least one actuator configured to receive the output control signal.

The present invention relates to a personal hygiene product that incorporates a digital element capable of interfacing with a smart hand-held electronic device, for example, a smartphone, a smart watch and/or a tablet. In accordance with one aspect, the electronic device may gather data received from each use of a personal hygiene product with a digital element or combination of hygiene products with digital elements.

In accordance with one aspect, the electronic device may comprise an event notification mechanism that may notify the user of an event that may occur, for example, within the personal hygiene product or an alert related to a biometric change. In accordance with another aspect, the electronic device may analyze and aggregate the data communicated from the digital element in the personal hygiene product to generate a report, summary, chart, or visual tool for the user, for example, reflecting menstrual flow patterns. The electronic device may provide a link for the purchase options of personal hygiene products based on data, for example, a home health program ordering weekly personal hygiene products for delivery to the user in the home.

In accordance with one aspect, the application or software may receive data from the digital element on the level of saturation of the personal hygiene product and absorbent capacity of the product while the user is wearing it. The application or software may signal the user through a warning or alert if and/or when maximum saturation will occur, so the user can change the personal hygiene product prior to leakage or spillage.

In accordance with one aspect, the application or software may use data gathered from each use of a personal hygiene product with a digital element to generate predictive analytics to advise the user of information related to the flow or discharge. Such an embodiment may, for example, provide a woman with information about her menstrual cycle such as her estimated start day and time of day. Such an embodiment may also, for example, provide a woman with information on what personal hygiene product level of absorbency is recommended for a given day in her menstrual cycle.

In accordance with one aspect, the electronic device may receive data from the digital element that convey personal health information such as body temperature for fertility monitoring or biometrics to indicate infection. Such an embodiment may, for example, allow a user to present data aggregated by the external electronic device to a primary care physician.

In accordance with another aspect, the application or software may use data gathered from the use of a personal hygiene product with a digital element to alert and/or mobilize facility resources to change the personal hygiene product. Such an embodiment, for example, may alert a nursing station and then a lifting team, that a personal hygiene product needs changing. Such an embodiment, for example, may also allow a facility to more accurately identify resources needed to best protect the health of patients, residents, or staff.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

A device comprising a personal hygiene product with a digital element capable of interface with a smart hand-held electronic device is disclosed in this specification. In the following sections, detailed descriptions of various embodiments are described. The descriptions of various embodiments are illustrative exemplary embodiments, and various modifications and alterations may be apparent to those skilled in the art. Therefore, the exemplary embodiments do not limit the scope of this application. The digital element is designed for use in or adjacent to the body of a living organism.

Glossary

In the description and claims below, various terms may be used for which the following definitions will apply:

"Biocompatible" as used herein refers to a material or device that performs with an appropriate host response in a specific application. For example, a biocompatible device does not have toxic or injurious effects on biological systems.

"Communication system" as used herein, may refer to a wireless communication device that can be configured to transmit and receive information from a processor to a receiver in a smart hand-held electronic device.

"Digital element" as used herein, may refer to electronic components on a substrate.

"Smart hand-held device" as used herein, may refer to a smartphone or tablet built on a mobile operating system and having advanced processing capabilities.

"Feminine hygiene product" as used herein refers to but is not limited to a tampon, sanitary pad, panty liner, or other product used to absorb or contain menstruation or bodily fluid discharge.

"Hygiene product" as used herein refers to any absorbent material or device used by adults to absorb or contain bodily fluid discharge, including tampons, liners, men's guards and shields, adult diapers and booster pads.

"Microfluidic analytical systems" as used herein may refer to a low energy consumption system including one or more pore(s) from which a fluid sample may be collected, and in some embodiments, moved through a channel or diffused, for the characterization of one or more properties of the fluid sample. In some embodiments, the microfluidic analytical systems can include microfluidic components, such as micro-pumps and micro-valves.

"Power source" as used herein refers to any device or layer which can supply energy or place a logical or electrical device in an energized state. The power source may include batteries. The batteries can be formed from alkaline cell chemistry and may be solid-state batteries or wet cell batteries.

"Sensor array" as used herein means a sensor or a plurality of sensors, which may include, for example, resistive or capacitive to detect liquid or moisture.

Figure 1:
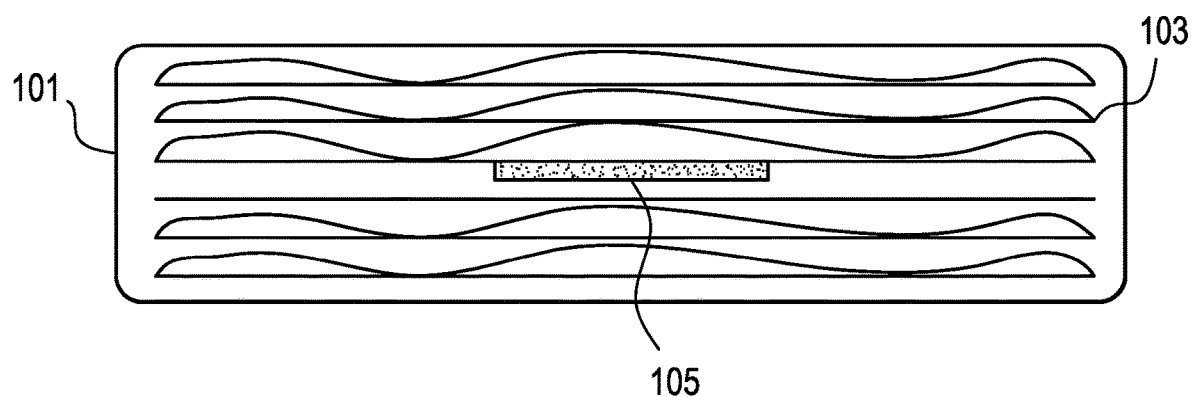
FIG. 1 illustrates an exemplary embodiment of a cross-section of a personal hygiene product with a digital element embedded within the absorbent materials of the product in accordance with the present invention.

"Switch" as used herein means a circuit element that controls the flow of electrical current in response to a physical or electrical input Personal Hygiene Product Referring now to FIG. 1, a cross-section of an exemplary embodiment of a personal hygiene product 101 with a digital element 105 is illustrated. The digital element 105 is embedded in the absorbent core 103 of the personal hygiene product that is inserted into or placed against a user's body. In some embodiments, the digital element 105 may be located on the body-side exterior surface of a personal hygiene product that is inserted into or placed against a user's body. In some embodiments, the digital element 105 comprises a substrate, comprising, for example, a biocompatible polymer or other flexible, biocompatible material, incorporated with electronic components for power, sensing, and communication.

Figure 2A:
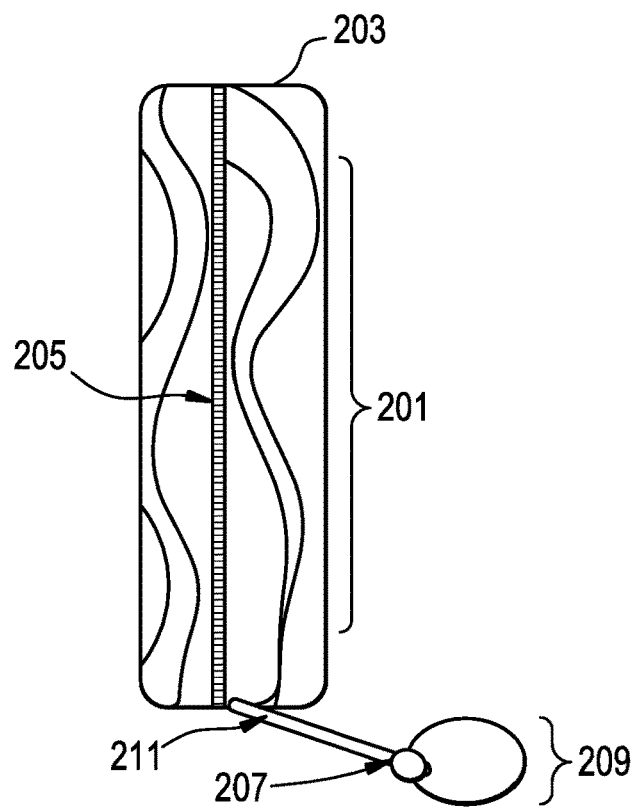
FIG. 2A illustrates an exemplary embodiment of a cross-section of a personal hygiene product with a digital element magnetically connected externally to the personal hygiene product with a conductive ribbon within the absorbent materials of the product in accordance with the present invention.
Figure 2B:
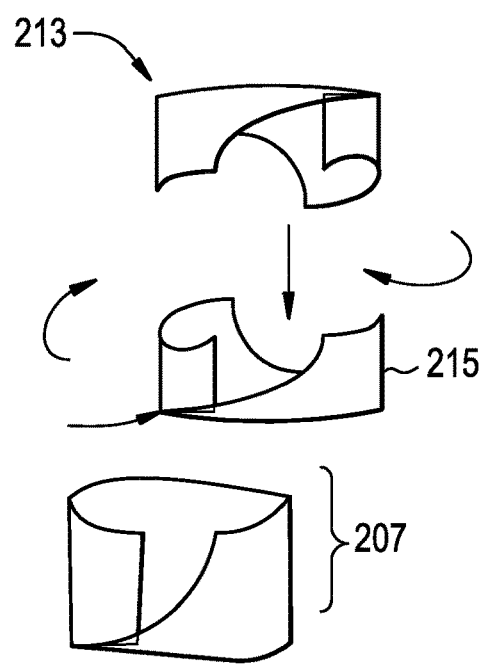
FIG. 2B illustrates an exemplary embodiment of a magnetic coupling component in accordance with the present invention.

Referring now to FIG. 2A, there is illustrated a cross-section of a personal hygiene product 201 with an external digital element 209 and a sensor assembly 205. The sensor assembly 205 comprising, for example, a sensor array, running through the center of the absorbent core 203 of the personal hygiene product 201 and connected to the external digital element 209. The sensor array 205 may comprise metalized fiber or may comprise conductive ink utilized in conjunction with the thread within the personal hygiene product 201. In some exemplary embodiments, the conductive ink may be printed on a substrate within the personal hygiene product 201. The sensor array 205 may be capable of sensing conductive and ionic properties of bodily fluids absorbed by the personal hygiene product 201. The sensor array 205 may capture resistive change in the personal hygiene product 201 as it becomes saturated with bodily fluids. The sensor array 205 is electrically coupled to external digital element 209 via signal transmission conduit 211. In some embodiments, the signal transmission conduit 211 may be magnetically connected to digital element 209. More specifically, a magnetic coupling device 207 may be utilized to connect the signal transmission conduit 211 to the digital element 209. For example, as illustrated in FIG. 2B, the signal transmission conduit 211 may include a magnetic coupling 213 on a first end and digital element 209 may include a mating magnetic coupling 215, which, when joined, form secure coupling 207.

Digital Element

Figure 3:
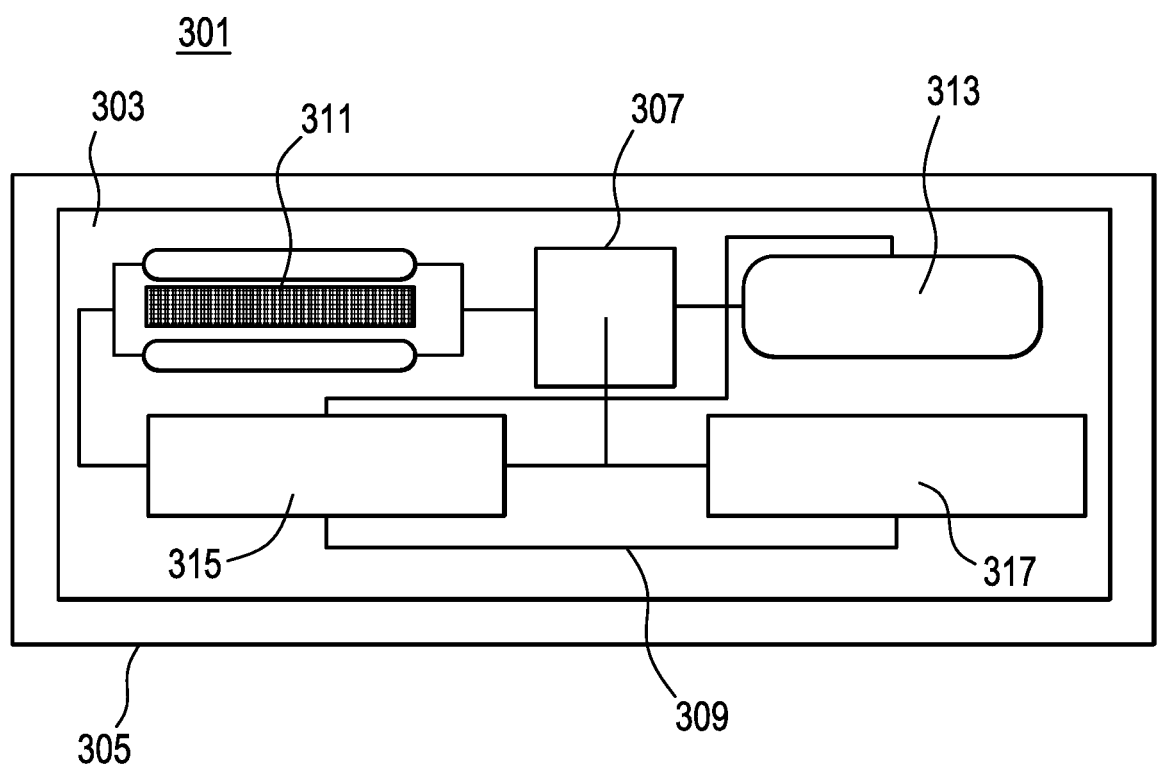
FIG. 3 illustrates a top down view of an exemplary embodiment of the digital element comprising a substrate embedded within the absorbent layers of the personal hygiene product in accordance with the present invention.

In FIG. 3, an exemplary embodiment of a digital element 301 is illustrated. In some embodiments, a substrate 303 is encased or encapsulated within a biocompatible polymer layer 305. In some embodiments, a power source 307, which may be, for example, an activation element or a battery, is attached to the substrate 303. The substrate 303 may comprise, for example, polyimide, cellulose Nano fibrillated fiber, or other biocompatible polymer or silicon. In some embodiments, conductive traces 309 may electrically interconnect the power source 307 with electronic components 311, 313, 315, and 317 collectively.

In some embodiments, the electronic components may include a sensor array 311 that comprises a single sensor attached to the power source 307 and a first processor 315 capable of data collection. The sensor or sensor array may, for example, include an optical sensor, an oximetry sensor, an electrical sensor, a chemical sensor, a mechanical sensor, a MEMs sensor, a nanosensor, a biochemical sensor, an acoustic sensor, an immunologic sensor, a fluidic sensor, or a "lab on a chip" type sensor.

In some embodiments, the electronic components may include a sensor array 311 attached to the power source 307 and a first processor 315. In some embodiments, the first processor 315 that collects data from the sensor array 311 communicates with a second processor 317 that is capable of wireless communication with a smart hand-held electronic device, which may be, for example, a smartphone, a smart watch and/or tablet. First and second processors 315 and 317 are preferably implemented in a single microprocessor.

In some embodiments, the electronic components may include a microfluidic analytical system 313 attached to a power source 307 that communicates with a first processor 315 that collects data. In some embodiments, the first processor 315 communicates with a second processor 317 capable of wireless communication with a smart hand-held electronic device, which may be, for example, a smartphone, a smart watch and/or tablet.

In some embodiments, the electronic components may include a sensor array 311 that may capture data regarding the liquid absorption capacity and saturation level of the personal hygiene product and communicate that data to a first processor 315. In some embodiments, the sensor array 311 may capture data regarding the absorption capacity of the personal hygiene product and communicate that data to the first processor 315. The first processor 315 may aggregate the collected data generated by the sensor array 311 and transmit the collected data to the second processor 317 that may wirelessly communicate the collected data to a smart hand-held electronic device.

In some embodiments, the electronic components may include a sensor array 311 that may capture biometric data, including, for example, temperature of the body, pH level, blood oxygen saturation, blood glucose levels, chemical composition, hormone levels, and body motion, and communicate that data to a first processor 315. The first processor 315 may aggregate the collected data generated by the microfluidic analytical system 313 and transmit the collected data to the second processor 317 that may wirelessly communicate the collected data to a smart hand-held electronic device by, for example, low power blue tooth wireless communication or near field wireless communication.

In some embodiments, the electronic components may include a microfluidic analytical system 313 that may capture data regarding biometrics, including, for example, the presence of harmful bacteria, hormone levels, cervical and uterine health indicators, or any cancerous markers, and communicate that data to a first processor 315. The first processor 315 may aggregate the collected data generated by the microfluidic analytical system 313 and transmit the data to the second processor 317 that may then wirelessly communicate the collected data to a smart hand-held electronic device.

Figure 4:
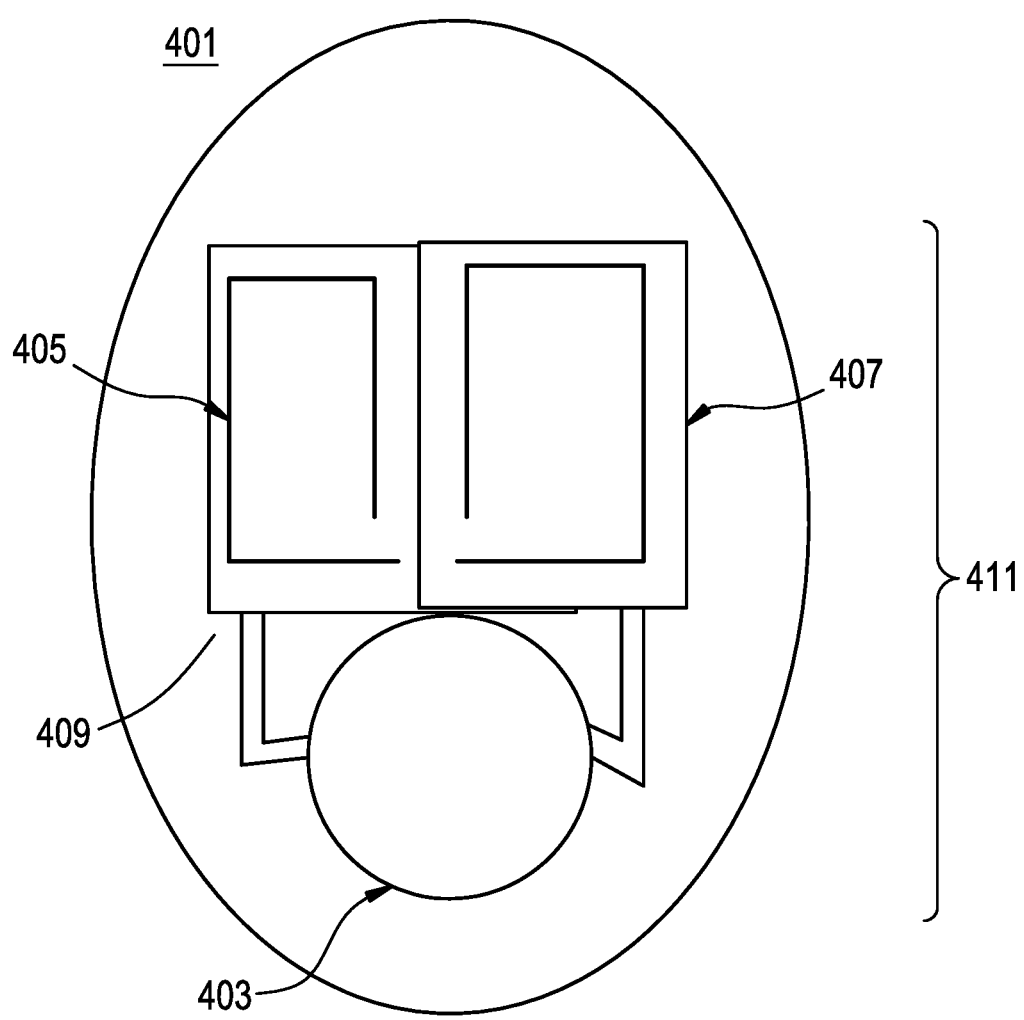
FIG. 4 illustrates a top down view of an exemplary embodiment of the digital element comprising an external substrate that connects to a conductive ribbon within the absorbent materials of the product in accordance with the present invention.

Referring now to FIG. 4, an embodiment of a reusable external digital element 401 is illustrated. The digital element attaches to the sensor array in the personal hygiene product by interlocking magnetic connection, such as that described above in connection with FIG. 2B. The digital element 401 may comprise a substrate 409 with electronic components 411 mounted thereon. The substrate 409 may comprise, for example, polyimide, cellulose Nano fibrillated fiber, or any other suitable biocompatible polymer. The digital element 401 may be encapsulated in a biocompatible material, for example, silicone. The electronic components 411 may comprise a communication circuit 405, a processor circuit 407, and a power source 403. The communication circuit 405 and processor circuit 407 may be, for example, a flexible or rigid thin printed circuit board. The communication circuit 405 may facilitate wireless communication with a smart hand-held device by, for example, low power blue tooth or near field communication. The communication circuit 405 may include an antenna comprising, for example, graphene or a bioabsorbable or biologically inert conductive ink. The processor circuit 407 may include a sensor array capable of processing data generated by the user's wear of the personal hygiene product. The power source 403 may be, for example, a battery, fuel cell or any other power source suitable for powering microelectronic components. Such suitable devices include, but are not limited to, lithium manganese dioxide coin cells.

Smart Hand-Held Device

Figure 5:
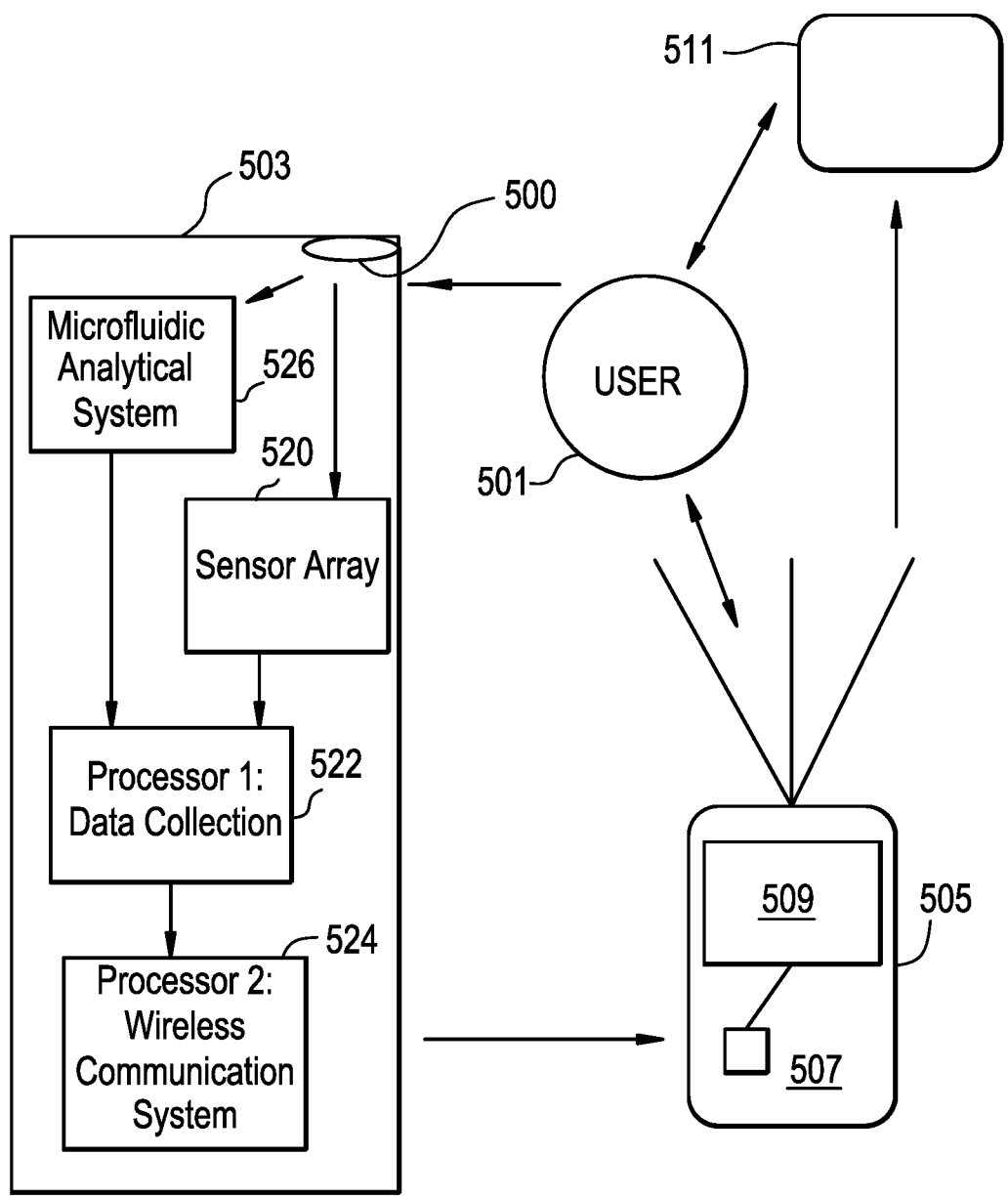
FIG. 5 illustrates a diagrammatic representation of the exemplary personal hygiene product with digital element detection path utilized to detect user data and wirelessly communicate that data to a smart hand-held electronic device in accordance with the present invention.
Figure 6A:
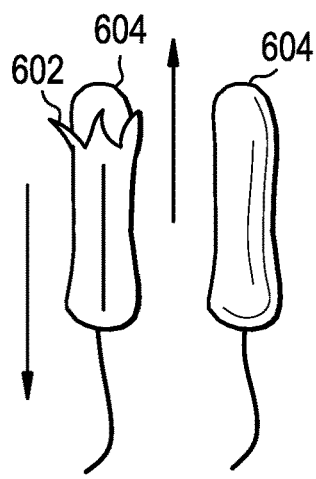
FIGS. 6A-6E illustrate exemplary embodiments of activating the digital element prior to use in accordance with the present invention.
Figure 6B:
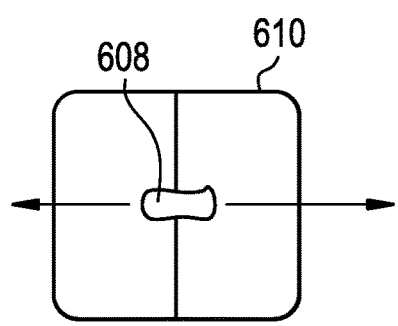
Figure 6C:
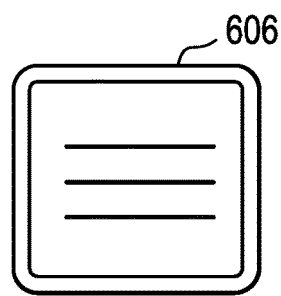
Figure 6D:
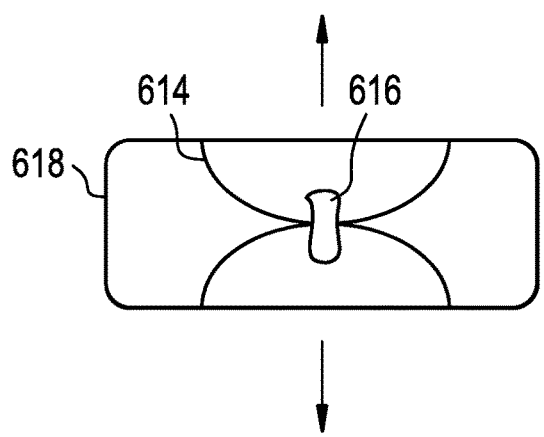
Figure 6E:
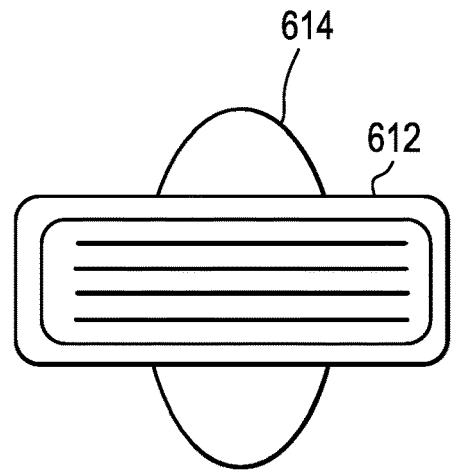

Referring now to FIG. 5, a diagrammatic representation of the digital element 503 and the interface with a smart hand-held device 505, and the interface of the smart hand-held device 505 with a user 501 and/or an internet-based consumer service 511 is illustrated. The smart hand-held device 505 may comprise a hand-held personal electronic device such as a cell phone, a smart watch and/or tablet.

In some embodiments, the digital element 503 is capable of wireless communication with a smart hand-held electronic device 505 that has a receiver 507. In some embodiments, the receiver 507 is capable of transmitting user-based data to a processor in the external device that may include, for example, a software application 509 capable of quantifying the user-based data. The user 501 may then interface with the external electronic device 505 and receive in some way the user-based quantified data.

In some embodiments, the software application 509 functions, may include, for example, an interface that quantifies the user-based data received and generates a visual representation of quantified data for the user 501, including, for example, generation of a chart, display, or alert for the user 501.

In some embodiments, the software application 509 may be able to provide the user with a visual representation of the level of absorption by the personal hygiene product based on liquid absorption capacity and actual body fluid absorption. In some embodiments, the software application 509 may be able to provide the user with a time frame for absorbency and anticipated saturation points. In some embodiments, the software application 509 may generate an alert signal to the user if saturation of the personal hygiene product is impending or reached. In some embodiments, the software application 509 may generate a visual representation of the quantified data, including, for example, the user's rate of bodily fluid discharge or historical data of bodily fluid discharge.

In some embodiments, the software application 509 may be capable of accumulating data generated over time from use of multiple personal hygiene products. In some embodiments, the software application 509 may be able to generate a graphic, chart, or other interface to illustrate a baseline for the body fluid discharge based on the historical data. In some embodiments, the software application 509 may be able to generate predictive analytics and communicate that information to a user. Such information may allow the user 501 to anticipate start and end dates, for example, if the personal hygiene product with a digital element is used for a menstruation cycle. Such information may allow the user 501 to understand the course of a cycle, including days or time periods of heavier or lighter flow.

In some embodiments, a software application 509 may generate information on a consumable usage rate for the user, predicting how many personal hygiene products are needed, including, for example, per day, per week, or per cycle. In some embodiments, a software application 509 may generate a reminder or warning for a user to purchase personal hygiene products, including, for example, where a start date for menstruation has been identified. In some embodiments, a software application may provide the user an order quantity estimation based on historical data of the user's bodily fluid discharge. In some embodiments, the interface of the software application 509 may provide a direct link to an internet-based consumer service where a user 501 may order and purchase additional personal hygiene products for direct delivery. In some embodiments, the software application 509 may be capable of automatic direct order placement based on consumable usage rate for delivery direct to user 501. The software application 509 may facilitate purchase of additional personal hygiene products. The software application 509 may connect the user to internet-based consumer services.

The digital element 503, as set forth above, comprises a sensor array 520, a first processor 522, a second processor 524 and a microfluidic analytical system 526. The digital element 503 is also illustrated as having a port 500 which allows fluid to enter and reach both the sensor array 520 and the microfluidic analytical system 526.

Tampon

Figure 7:
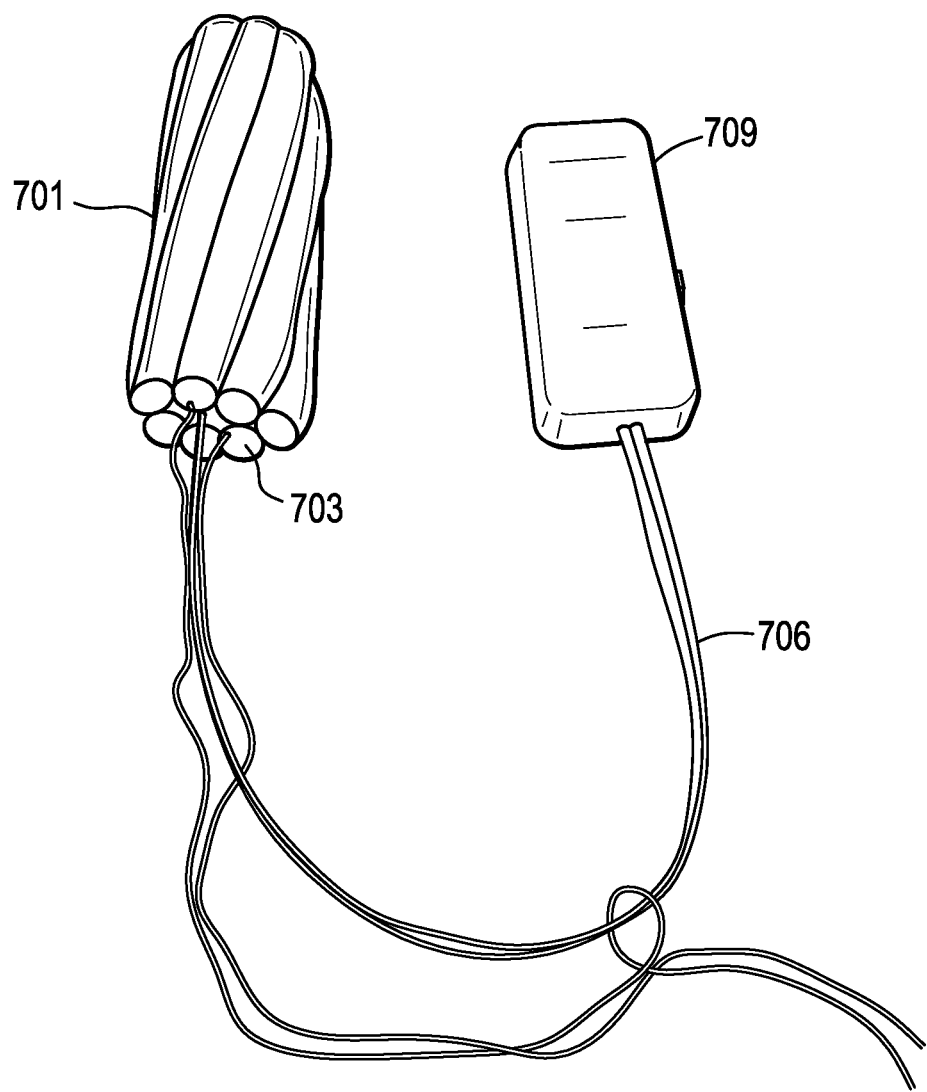
FIG. 7 illustrates a personal hygiene product coupled to a digital element in accordance with an exemplary embodiment of the present invention.

In accordance with one exemplary embodiment of the invention, a personal hygiene product 701 in the form of a tampon with a digital element is provided. Referring to FIG. 7, the personal hygiene product 701 is coupled to an external digital element 709 via a signal transmission conduit 706. Disposed within personal hygiene product 701 is a conductive sensor assembly (not shown in this figure), for example, running through the center of the absorbent core 703 of the personal hygiene product 701.

Figure 8:
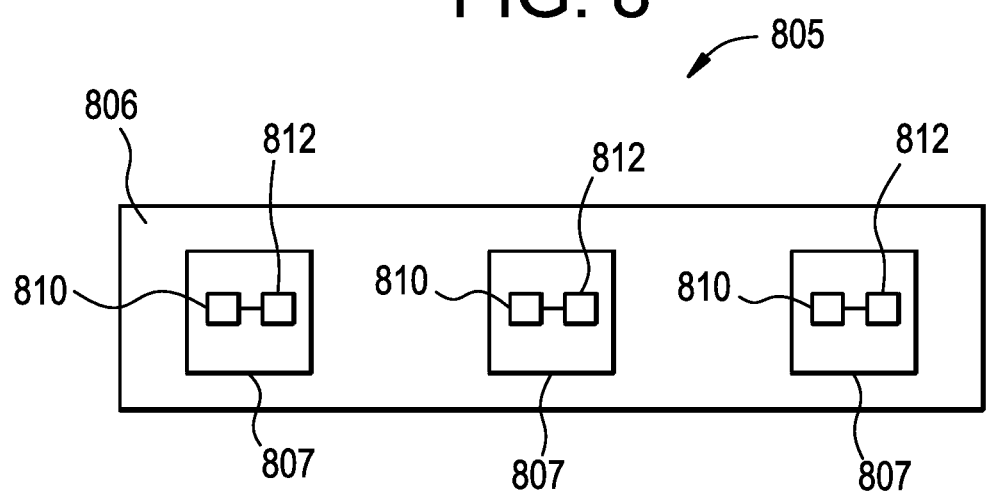
FIG. 8 depicts a sensor array in accordance with an exemplary embodiment of the present invention.

In at least one embodiment, as illustrated in FIG. 8, a conductive sensor assembly 805 generally comprises one or more moisture sensors 807 that may be capable of sensing conductive and ionic properties of menstrual fluid by, for example, measuring resistance. Moisture sensors 807 are disposed on a substrate 806 that may comprise PET, polyimide, cellulose Nano fibrillated fiber, or other biocompatible polymer or silicon. In some embodiments, the substrate may comprise a flexible circuit board. Each moisture sensor includes a moisture sensitive switch 810 coupled to a resistor 812. Moisture sensitive switch 810 is configured to conduct or "turn on" when in wetting contact with menstrual fluid and thus generate a signal indicative of the saturation level of the personal hygiene product.

Figure 9:
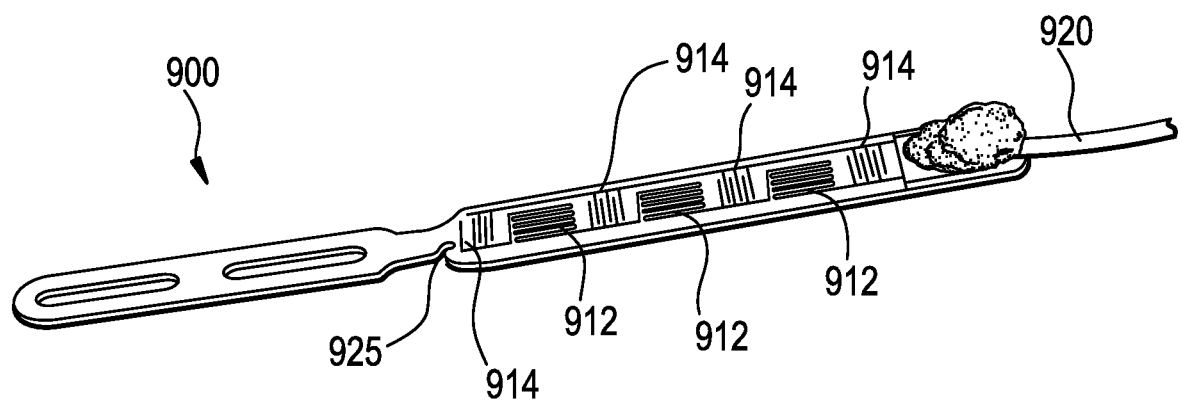
FIG. 9 illustrates an exemplary sensor assembly in accordance with the present invention.

FIG. 9 illustrates a conductive sensor assembly 900 including resistors 912 connected to moisture sensitive switches in the form of interdigitated electrode patterns 914. The presence of salt and other ionic constituents of the menstrual fluid between and around interdigitated electrodes 914 facilitates conductivity between interdigitated electrodes 914. In the absence of menstrual fluid, there is no statistically significant conductivity between interdigitated electrodes 914. Essentially, when there is no fluid present and all is dry, there is no conductivity. A signal transmission conduit 920 is provided to carry the signal transmitted by the moisture sensitive switches to the digital element. In some embodiments, signal transmission conduit 920 may be a cable connected to a digital element such as that described above in connection with FIG. 4. In some embodiments, transmission conduit 920 may comprise conductive ink deposited on a flexible substrate. Resistors 912 may be formed from conductive ink deposited on substrate 925. In some embodiments, where the substrate 925 is a flexible circuit board, resistors 912 may be on board resistors.

It is believed that the constituents of menstrual fluid vary widely from subject to subject. Accordingly, conductivity of menstrual fluid may well vary by as ±50 percent or more from subject to subject due at least in part to differing ionic content as well as other factors. This conductivity inconsistency across subjects may cause moisture sensors to behave differently for different subjects. For example, due to the differences in menstrual fluid conductivity, a moisture sensor may indicate that a personal hygiene product used by a first subject is saturated and fail to indicate that a personal hygiene product used by a second subject is saturated when both personal hygiene products are exposed to identical amounts of menstrual fluid. To provide more consistent results from subject to subject, in some embodiments resistance values for resistors 812 and moisture sensitive switches 810 are selected to minimize the impact of menstrual fluid conductivity variation. Accordingly, the resistance of resistors 812 is preferably much greater than the resistance of moisture sensitive switches 810. In some embodiments resistors 812 may have a resistance value between 1 kΩ and 10 kΩ. However, these resistance values may be tuned to cause the personal hygiene product to behave in a specifically desired manner.

In some embodiments, conductive sensor assembly 805 may extend generally the entire axial length of the tampon to detect saturation at various points along the axial length of tampon. In some embodiments, conductive sensor assembly may include only a single moisture sensor positioned at point along the tampon which indicates full saturation of the tampon. In other embodiments, moisture sensors may be positioned at various points along the axial length of the tampon, e.g., 10 percent, 50 percent, 75 percent and 90 percent.

In accordance with an alternate exemplary embodiment, the sensor system of the present invention may be or comprise a capacitance sensor rather than a resistive sensor. An exemplary capacitance sensor may comprise at least a pair of linear conductive leads spaced from each other and configured to generate an electric field between each other when an electric potential is applied across the conductive leads. The conductive leads may comprise one or more of a conductive wire, a conductive thread, or a conductive yarn. The conductive yarn may comprise a yarn that has been treated (e.g., covered) with a conductive material. The conductive thread may comprise a thread that has been treated (e.g., covered with a conductive material).

The capacitance sensor may comprise an insulator. The insulator may be one or more of hydrophilic, hydrophobic, omniphilic, omnophobic, oleophilic, or oleophobic. For example, the insulator may be treated to cause a surface of the insulator to be one or more of hydrophilic, hydrophobic, omniphilic, omnophobic, oleophilic, or oleophobic. The insulator may be disposed between an absorbent material and at least a portion of each of the conductive leads. As an example, an electrically insulative material may be disposed about at least a portion of each of the linear conductive leads. As such, the insulative material may be disposed between each of the linear conductive leads. The insulative material may also insulate the linear conductive leads from the absorbent material of the personal hygiene product. Accordingly, when electrical current is applied to one or more of the linear conductive leads, an electric field is generated between the linear conductive leads. The linear conductive leads and the electrical current are configured such that at least a portion of the generated electric field passes through the absorbent material. As a fluid level (e.g., saturation) of the portion of the absorbent material in the generated electric field changes, electrical characteristics (e.g., capacitance) of the dielectric or other materials in the field may change. Such a change may be measured and may be indicative of the fluid level of the personal hygiene device incorporating the sensor system. As an example, the sensor system may be configured to detect a first capacitance value and a second capacitance value that is different from the first capacitance value.

In an alternate exemplary embodiment, a capacitance sensor may comprise a capacitance and a resistive component. In this embodiment, the ends of a parallel joined section are left un-insulated. With the parallel section folded on itself as it is placed in the tampon or other product, the two open conductive ends are at the base of the tampon. When the tampon is full, these two conductive ends will short with menstrual fluid and this is detected by the resistive sensing component. This arrangement may be utilized as a back-up or leak warning due to possible bypass of fluids.

A controller may be integrated with or configured to communicate with the sensor system (e.g., capacitance sensor). As measurement of electrical characteristics of the capacitance sensor is made, a signal may be transmitted to the controller. The signal may be indicative of one or more of a first capacitance value and a second capacitance value. As described herein, the first capacitance value and the second capacitance value may be dependent upon the presence of a fluid within the electric field between the linear conductive leads when electric current is applied to one or more of the linear conductive leads. The controller may be configured to analyze the received signal and may determine an associated fluid level (e.g., saturation). Such determination may be an absolute or relative determination. Moreover, the controller may communicate the associated fluid level to a user of the device, for example, via a user interface.

Operation

Referring now to FIGS. 6A-6E, a diagrammatic representation of the activation of the digital element in the personal hygiene product is illustrated as the opening and use of the items. In operation, a user may use the personal hygiene product in a manner consistent with industry use, including, for example, insertion into the body, FIG. 6A, placement directly against the body, FIGS. 6B and 6C, or adhesion to an undergarment and placement directly against the body, FIGS. 6D and 6E. The user may, prior to placement or insertion of the product near or in the body, activate the digital element by unfolding or pushing the product through an applicator. When the digital element has been activated, the user may then place or insert the personal hygiene product. With respect to FIG. 6A, the wrapper 602, which is positioned on the tampon 604, is removed and the tampon 604 itself may be inserted in the usual manner. More specifically, the wrapper is formed and placed on the tampon and then the ends are sealed. With respect to FIGS. 6B and 6C, a pad or sanitary napkin 606 is removed from the packaging 610 by removing the top tab 608 and then positioned in the usual manner. With respect to FIGS. 6D and 6E, the pad or sanitary napkin 612 is removed from its package 618 by removing the tab 616 and unfolding adhesive tabs 614. The adhesive tabs 614 are secured in position to an undergarment, not illustrated in this figure, in the usual manner.

Figure 10:
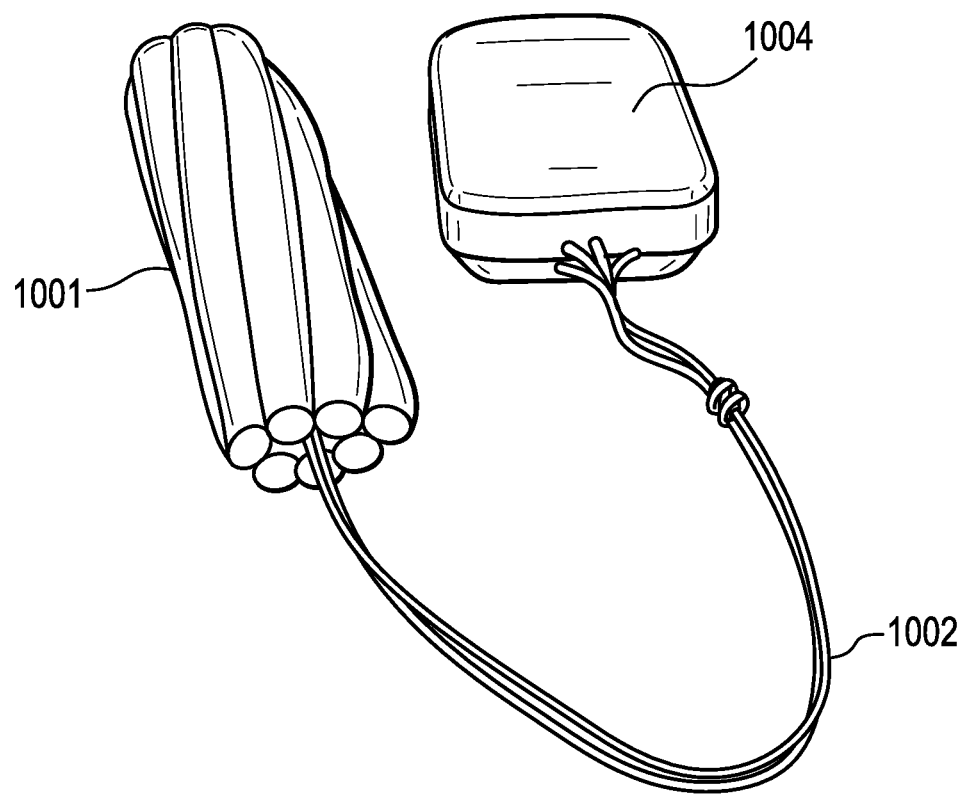
FIG. 10 illustrates an exemplary tampon with embedded sensor, leads, and connection to a signal acquisition device in accordance with the present invention.

In accordance with another exemplary embodiment, the present invention comprises connectors and encasements for use with the personal hygiene products described herein. Electronic feminine hygiene systems have been previously explained. One such system is explained here with additional detail. FIG. 10 illustrates an exemplary tampon 1001 with an embedded moisture sensor or digital element, not illustrated in this figure, with leads 1002 coming out of the tampon 1001, and connected to a signal acquisition device within a case or enclosure 1004. In this example, the signal acquisition device performs a measurement utilizing the moisture sensor within the tampon 1001, for example capacitance, resistance and/or voltage, and transmits this data or information to a smartphone or similar personal electronic device. In this example, the embedded moisture sensor, not shown in this this figure, is manufactured from the same conductive yarn as shown in the leads 1002. The leads 1002, as explained in greater detail subsequently, may be made of conductive thread or conductive thread woven into non-conductive thread. The leads 1002 are mechanically and electrically connected to the signal acquisition device through a connector in the signal acquisition device. The connector, electronics, battery, antenna, and other components of the signal acquisition device are housed in the case or enclosure 1004 as described herein.

Figure 11A:
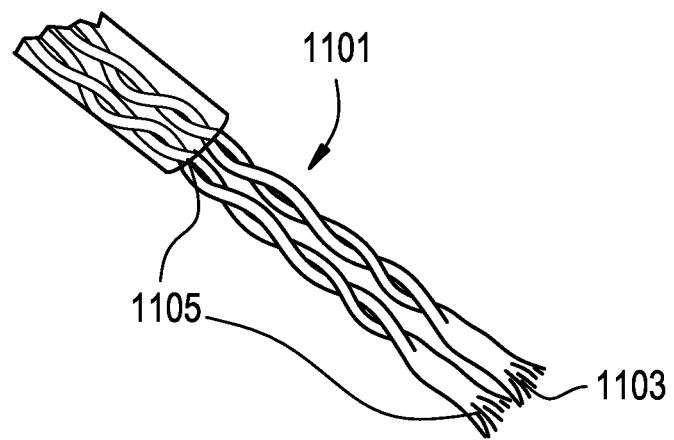
FIGS. 11A and 11B illustrate exemplary end termination methods for the tampon sensor connection to the signal acquisition device in accordance with the present invention.
Figure 11B:
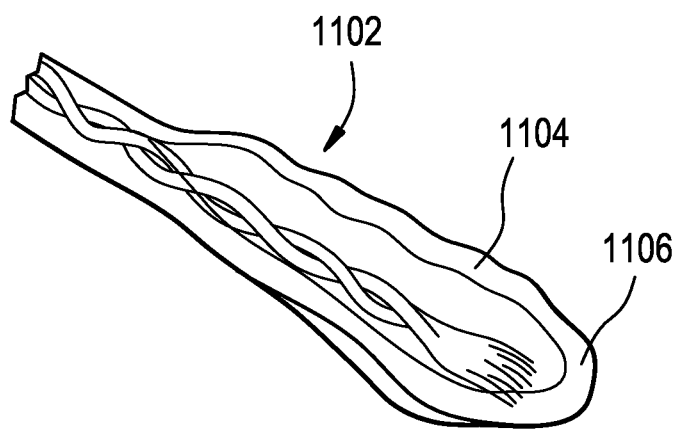

The way the leads from the sensor are terminated is of critical importance to the manufacturing, reliability, ease-of-use, and customer acceptance of an electronic feminine hygiene system. Exemplary termination methods are illustrated in FIGS. 11A and 11B, including unstripped, stripped, and flattened terminations. FIG. 11A illustrates an exemplary lead 1101 that is stripped of its insulation over a specified length 1105 and having flattened terminations or ends 1103. In this exemplary embodiment, the flattened terminations 1103 make direct contact with the acquisition device. The unterminated example, illustrated in FIG. 11B, leaves the wire/yarn 1102 as presented on the spool such that the inner conductor is covered by insulation 1104 except for at the ends (not shown). Such a termination method may require a piercing connector to puncture the insulation and make contact with the inner conductor. In other words, the electrical contacts of the contact pierce the insulation and make non-destructive contact with the inner conductors of the acquisition device. This termination method may be preferred due to ease of fabrication. In an alternate exemplary embodiment, utilizing heat and pressure, the insulation may be pressed away from the conductor exposing the conductive threads. With ends prepared this in this manner they may be placed in a compression type connection point without the need for piercing. These pressed ends can be applied directly to conductive plates on the surface of a Bluetooth device and covered with adhesive tape. This tape may then be applied to the user's skin or clothing.

In the stripped example, insulation is removed from a specified length 1105 of the wire/yarn to expose the inner conductor. Such a termination method may preclude the need for a piercing connector and reduce the diameter of the connector but may also introduce issues with shorting between the conductors.

In the flattened example, the insulation is redistributed through an operation such as pressing, heating, and/or ultrasonic energy. The resulting termination may or may not expose the inner conductor. It may also cause the insulation to wrap around the exposed end 1106, fully insulating it.

A treatment may be applied to the end termination with some dependence on the physical termination method employed. For example, an unstripped connection may be dipped in conductive adhesive, ink or epoxy. This would allow electrical contact over a wider area of the termination and may preclude the need for a piercing connector. A termination may also be dipped in a non-conductive adhesive or epoxy as an insulator. A termination may be crimped or glued onto the wire/yarn.

It may also be preferred to present both leads to the connector together instead of as two discrete leads. Although this may require a termination or crimping operation, making one connection instead of two is likely preferred by customers. Such a termination may use a discrete, crimped-on connector but such a solution adds the cost of the termination component. Another option, similar to the flattened connection, may be to join the lead ends without requiring a costly component.

Figure 12A:
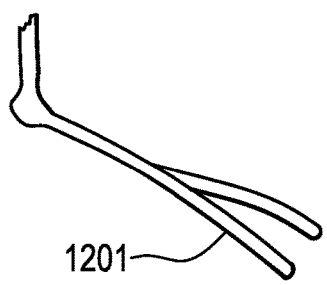
FIGS. 12A and 12B are a diagrammatic representations of exemplary connection end length mismatches presented to the signal acquisition device connector in accordance with the present invention.
Figure 12B:
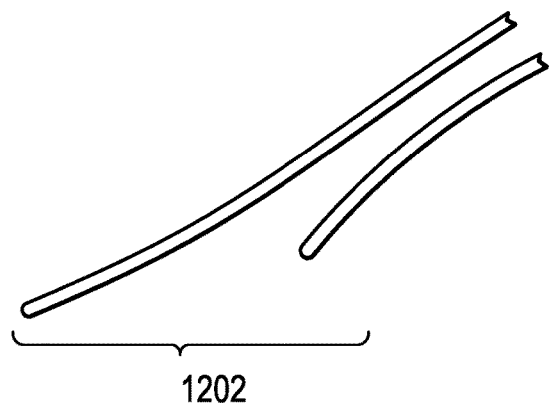

FIGS. 12A and 12B illustrate two exemplary embodiments for the lengths of the two wires/yarns presented to the connector by the sensor. In one case, illustrated in FIG. 12A both ends of the wire/yarn 1201 are roughly the same length. This may be a preferred case due to the optimizations it affords the connector, for example, the connector does not have to accept a wide variation in length. However, variation in length may arise from a manufacturing process and may be desired as a tradeoff with other parameters like cost, yield, and throughput. Accordingly, it may be desired to accept different length wires/yarns 1202 as illustrated in FIG. 12B. This may be accomplished by extending the length and area of the connector, but this comes with a tradeoff on overall connector size as well. It may also be possible for the connector to contain a "funnel" design to allow for lateral variation in the position of the lead, and/or to allow for the lead to fold inside the connector to absorb excessive length.

Figure 12C:
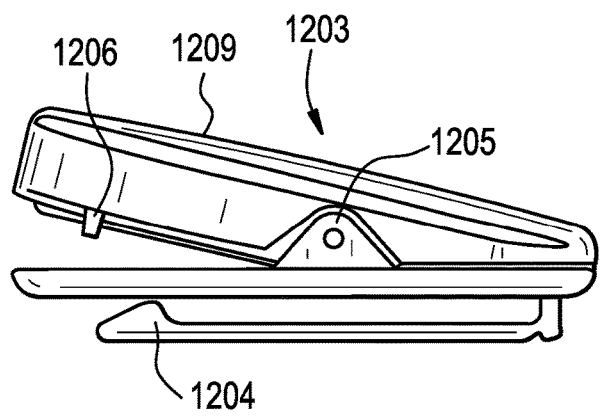
FIGS. 12C and 12D are diagrammatic representations of an exemplary signal acquisition device and connector, shown from two perspectives, in accordance with the present invention.
Figure 12D:
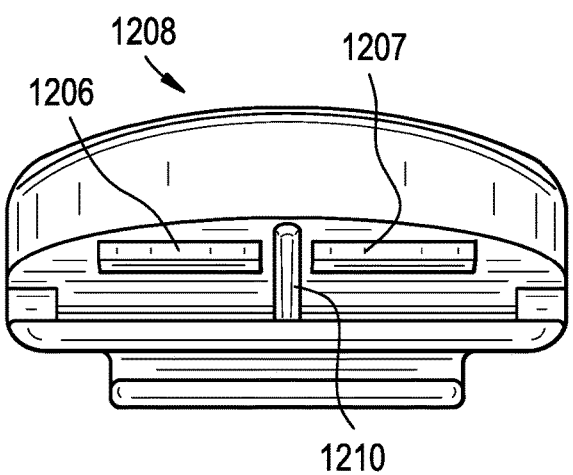

FIGS. 12C and 12D illustrate an exemplary enclosure and connector from two perspectives. The side perspective 1203 illustrates design aspects including a clip 1204 which may be suitable for attachment to an undergarment waistband. In addition, this device may also be worn or attached to an outer garment waistband. It may be attached to any suitable piece of clothing. Also shown is hinge 1205 which allows the top portion 1209 of the device to tilt thereby exposing the connectors 1206, 1207. In the front perspective 1208, side-by-side connectors 1206 and 1207 are shown with an insulator 1210 positioned therebetween. The two conductors from the sensor leads, FIGS. 11A and/or 11B, would be inserted into these connectors, perhaps by tilting the hinge, placing in the leads, then allowing a spring-loaded hinge to tilt back onto the leads, thereby retaining them. This arrangement is known in the electronics field.

Figure 13A:
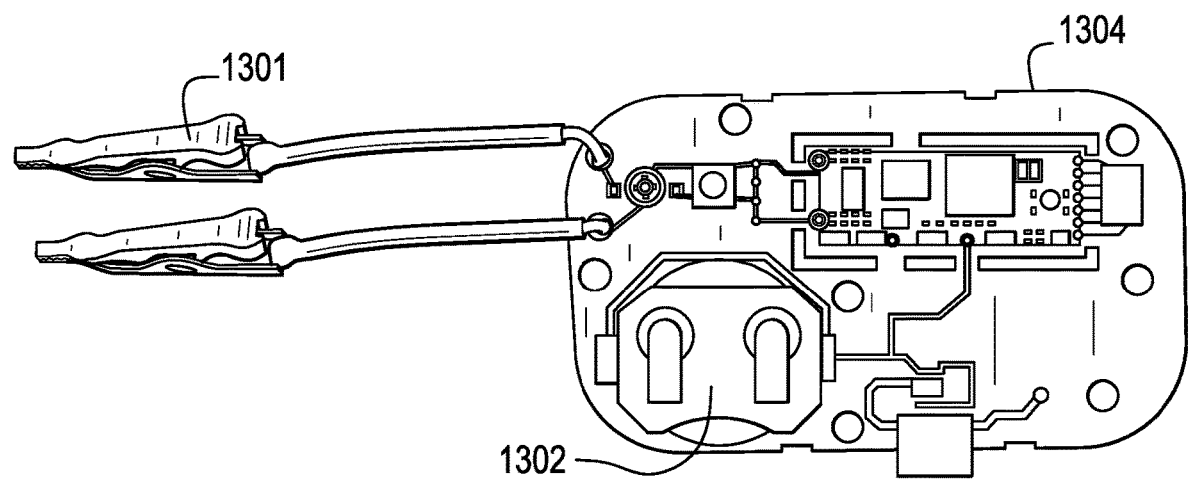
FIG. 13A illustrates a first commercially available connector and battery clip.

FIG. 13A illustrates another exemplary "off-the-shelf" connector 1301 and a battery clip 1302 mounted to a circuit board 1304 with various other electronic components. As discussed herein, novel devices are required due to shortcomings in existing devices such as described herein. The alligator clips 1301, while being useful for prototype testing, are too large for integration into an intimate consumer device. They are also easy to electrically short and intimidating to potential users. The battery clip 1302 requires insertion and removal to happen along one edge of the clip and this may not be a convenient operation for users.

Figure 13B:
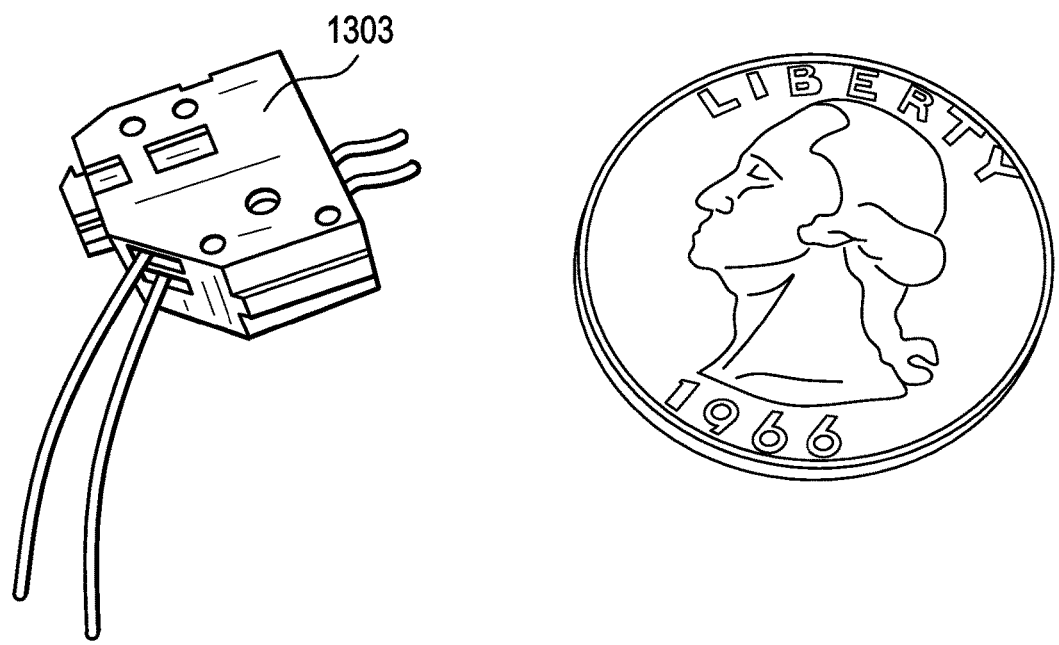
FIG. 13B illustrates a second commercially available connector.

FIG. 13B illustrates yet another "off-the-shelf" connector 1303. As may be seen from the scale of the inserted wire and adjacent the United States quarter, the connector 1303 is much larger than both the wire to be connected and the desired size of a discrete device. It is important to note that these illustrated connectors are existing connectors with no modifications that may be utilized but are by no means preferable.

Figure 14A:
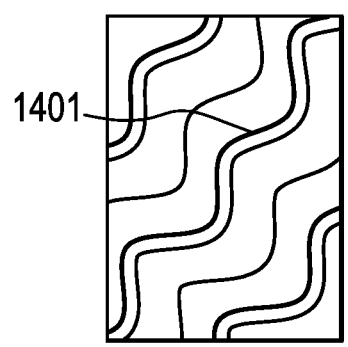
FIG. 14A is a top view diagrammatic representation of an exemplary modified surface a connector in accordance with the present invention.
Figure 14B:
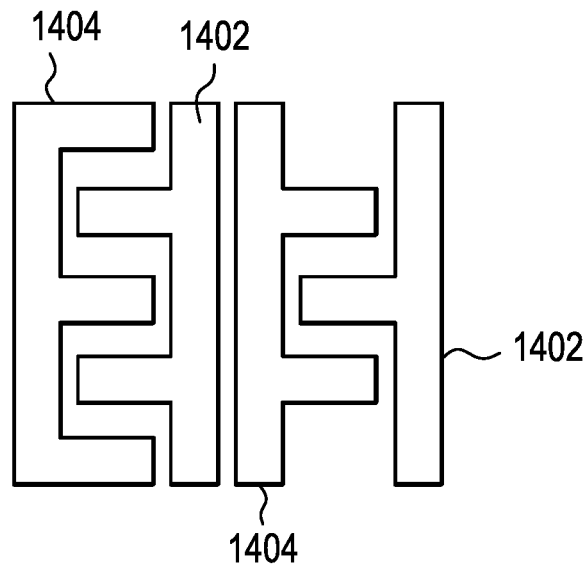
FIG. 14B is a side view diagrammatic representation of an exemplary interlocking connector in accordance with the present invention.

FIGS. 14A and 14B illustrate examples of connector design aspects to aid in lead retention. FIG. 14A illustrates a surface or "top-down" view onto the plane of a connector. The sensor lead would be laid on top of this plane. The plane illustrated includes wave-shaped texture 1401 to aid in retention of the leads regardless of insertion direction. An untextured surface or one in which the direction of texture is parallel to the lead may offer less retention force and less electrical reliability. Knurling is a known technique for increasing the "grip" of a connector. By making one or both planes of a connector with a textured surface increased friction preferably reduces the thickness of any connector utilized.

FIG. 14B illustrates the side view of an exemplary connector. In this example, two combinations of interlocking "top and bottom" surfaces are shown 1402 and 1404 respectively. When interlocked by external force, for example a magnet or spring, the "teeth" of the connector engage with a small gap between the pieces. A wire or yarn placed between the interlocking pieces may be bent around the corners, thereby increasing retention force and electrical reliability.

Figure 14C:
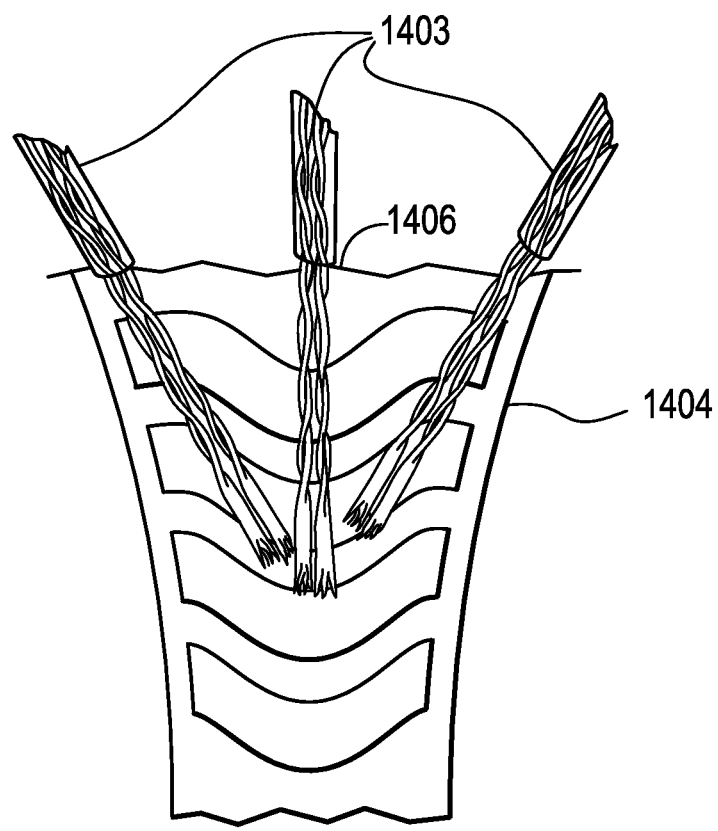
FIG. 14C is a diagrammatic representation of exemplary insertion positions for the connector, end termination, and position in an enclosure in accordance with the present invention.

FIG. 14C illustrates an exemplary orientation of a lead 1403 into a textured connector 1404. Various insertion angles increase user convenience and are afforded by the textured connector surface. Due to the shape of the textured connector 1404 any lead 1403 would be guided to the center 1406 regardless of the angle of insertion.

Figure 15A:
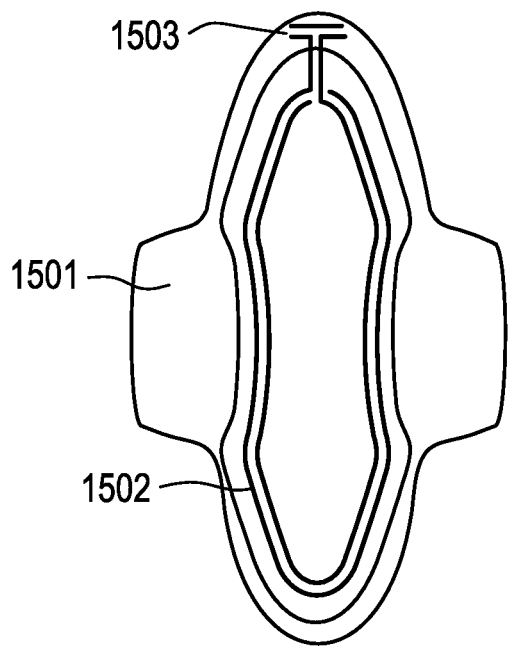
FIG. 15A is a diagrammatic representation of an exemplary feminine napkin with sensor in accordance with the present invention.
Figure 15B:
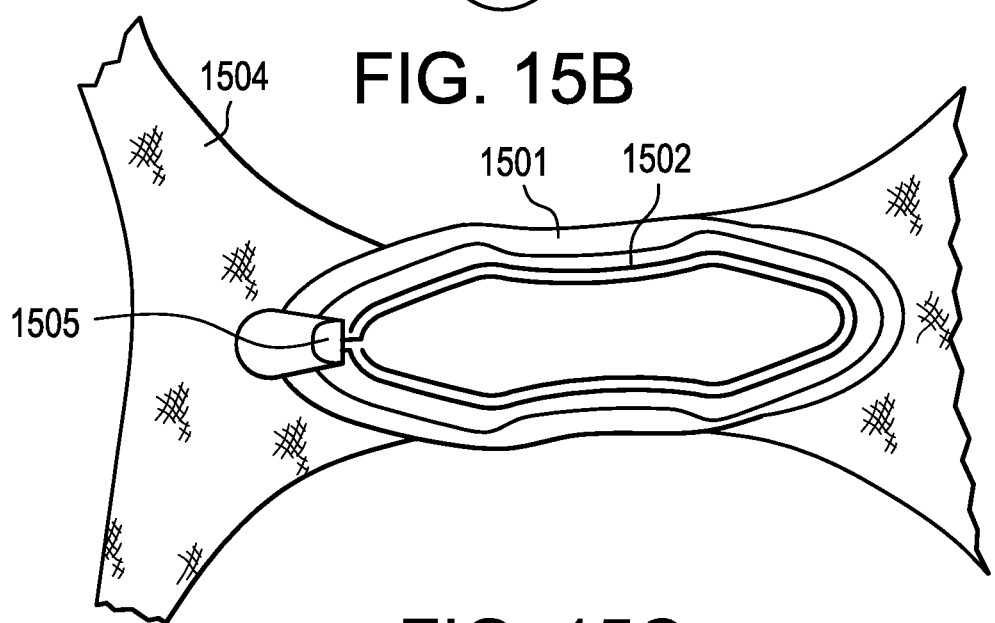
FIG. 15B is a diagrammatic representation of an exemplary attachment of a signal acquisition device to a feminine napkin and placement in underwear in accordance with the present invention.
Figure 15C:
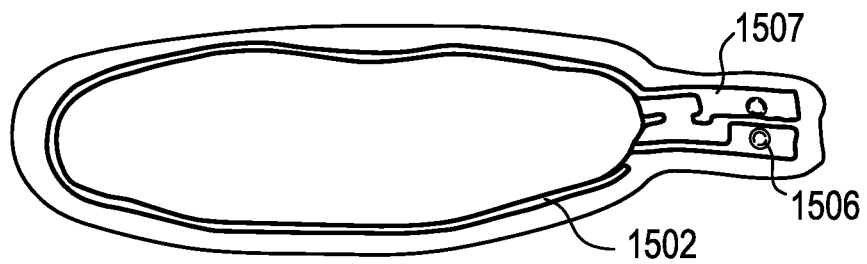
FIG. 15C illustrates an exemplary connector utilizing button snaps in accordance with the present invention.

FIGS. 15A-15C illustrate an alternate exemplary electronic feminine hygiene system with sanitary napkins rather than tampons. FIG. 15A illustrates an exemplary napkin 1501 with embedded sensor electrodes 1502. Such electrodes 1502 may be fabricated with conductive ink, metallized and transferred onto the pad, or through other methods. The ends of the electrodes 1502 form a connection point 1503. FIG. 15B illustrates the napkin 1501 with a signal acquisition device 1505 attached to connector point 1503, with both positioned on or against an underwear garment 1504. FIG. 15C illustrates an exemplary connector 1506 in which metal button snaps are crimped onto extended conductive traces 1507 on the napkin. These extended conductive traces 1507 connect to conductive traces 1502 and may contain features appropriate for attaching the snap connectors 1506 such as thicker and wider conductors.

Figure 16:
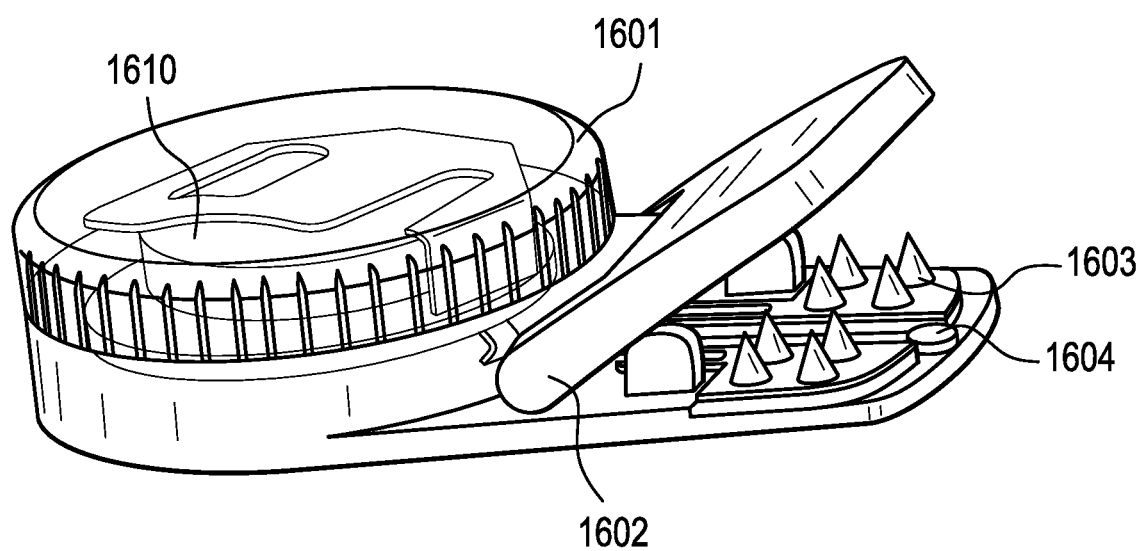
FIG. 16 is a diagrammatic representation of an exemplary case for the signal acquisition devices in accordance with the present invention.

FIG. 16 illustrates and exemplary case/enclosure systems for the signal acquisition device. A screw-top lid 1601 allows for replacement of a primary battery 1610 and may afford access to other components such as a reset or pairing button. The lid 1601 may comprise a gasket to improve water resistance. Such a gasket may be a discrete design like an O-ring or may be a soft, rubber- or silicone-like material co-molded or applied to the harder injection-molded plastic case. Instead of a gasket, an interference fit may be used in which attachment of the lid forms a compression fit sealing out water. It is important to note that water resistance is desired, not necessarily a waterproof design. There are varying degrees of water resistance, for example, just tolerating high humidity or a splash, very shallow and temporary immersion such as accidental exposure, shallow immersion lasting for minutes or hours such as pool swimming, and all the way up to deep-water immersion such as in scuba diving. Also illustrated is a hinged connector door 1602 which, as previously mentioned, allows for convenient engagement of the sensor leads to the signal acquisition device. Piercing connectors 1603, as previously described, are shown which may improve mechanical and electrical engagement both for tampon and napkin connectors. Such piercing connectors must be designed to 1) reliably pierce an insulated conductor and achieve a repeatable electrical and mechanical connection while simultaneously 2) not being intimidating or potentially harmful to the user. Such a tradeoff may be achieved by carefully designing the geometry of the piercing protrusions, e.g. the height, width, and sharpness of the points given the properties of the insulated yarn/wire, along with the properties of the connector such as the maximum opening size. Such a design may only allow a small wire to enter and prevent a finger, hair, or other body part from entering the connector. Also shown in a magnet 1604 which may attract a component of the lid, apply a force to squeeze the connector closed, and thereby improve mechanical retention.

It is greatly preferred that connectors for digital feminine hygiene systems operate with both tampons and napkins from one signal acquisition device. Over the period of a menstrual cycle, many users will switch between tampons and napkins, or perhaps use both simultaneously for an added degree of assurance. Users may prefer one signal acquisition device instead of having to keep track of multiple, sensor-specific devices. As shown in the figures, one sensor connection may have round leads while the other may be flat. One solution is to force both sensors to have similar leads, but this may not be preferred for user convenience, performance, cost, or other factors. A device connector that accepts both terminations may be greatly preferred.

Figure 17:
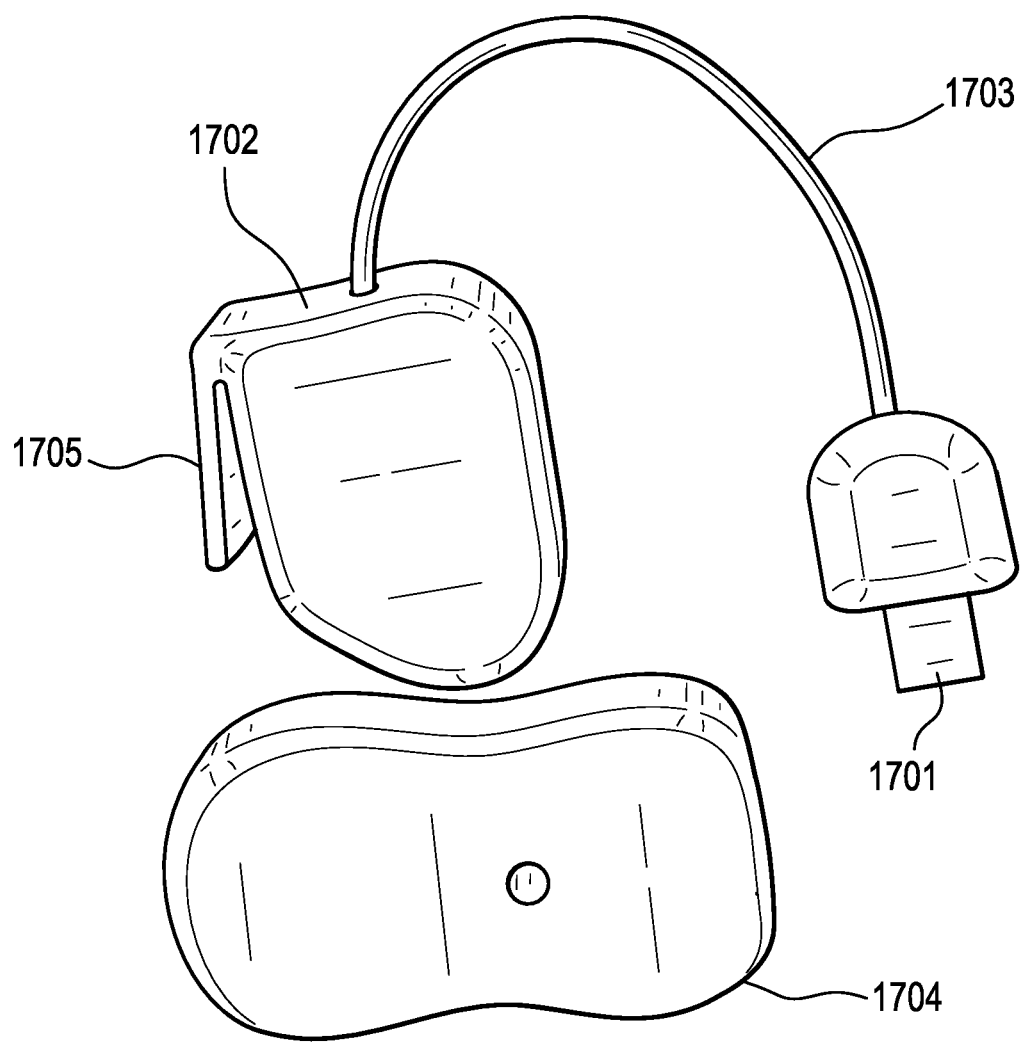
FIG. 17 is a diagrammatic representation of an exemplary extension device to be placed between the sensor and signal acquisition device in accordance with the present invention.

FIG. 17 illustrates an exemplary connector extension, in this case fabricated from an off-the-shelf female connector (not shown but contained within housing 1702) and a flex-based male connector 1701. Male connector 1701 may plug into a female receptacle in signal acquisition device 1704 thus allowing a sensor with limited connector length (not shown) to interface with a signal acquisition device located farther from the sensor. Such an extension may improve the convenience of the system by affording users placement of the signal acquisition device farther from the sensor, more room to make the connection, and the like. Such an extension may also minimize usage of relatively expensive sensor wire/yarn by allowing replacement by less expensive materials. An extension connector may also maximize the portion of the leads controlled and/or shielded and minimize the portion of the leads subject to introducing variations in capacitance, for example, due to body movements and the associated changes in conductor positions relative to each other and to the body. Housing 1702 may include feature 1705 to allow pressing a release actuator on a female connector within the housing 1702 or to clip housing 1702 to an undergarment.

It may be desired to provide a positive engagement signal to the user when a successful connection is made. This may include a tactile feedback, click, change in pushback force, and the like. This may be implemented through a spring and cam setup. It may be desired for the connector to automatically trigger certain actions in the signal conditioning device upon contact, engagement, or finalization of the connection. For example, insertion of sensor leads may trigger a calibration operation to "zero out" capacitance, perform a self-check, and send an indication to the user of sensor readiness.

The connector may be engaged and disengaged through a number of manners, for example a combination of press-to-open and press-to-release designs.

Instead of placing a discrete connector in an electrical enclosure, a preferred embodiment is to integrate the connector with the case utilizing techniques such as injection molding, co-molding, metal molding, and post processing. Metal deposition followed by electroplating may be necessary to achieve the desired metal, thickness, and surface finish. Metal alloys may be used to achieve the desired properties such as conductivity and resistance to chemicals.

An electrical button may be required to allow a user to perform a number of functions on the device, for example, waking up, putting to sleep, changing mode, resetting, and/or pairing with a Bluetooth device. Such a button introduces challenges to both size and water resistance for such a small device. The button may be "hidden" inside the battery compartment, thereby placing it inside a water-resistant environment, but such button location would not be easy to use for the patient. Similar to the connector and battery, a discrete button device may not be preferred due to the added cost and size. An electrical button may be integrated into the case using techniques as previously described, for example, co-molding and metal-plastic co-fabrication techniques.

Comfort of the device to be worn up against the body is of critical importance for customer acceptance. Some users may have particularly sensitive skin, and the device must be wearable for hours during activities that may include sitting, standing, exercising, and the like. The material in contact with a user's body should be soft and smooth, thin, promote a favorable tactile response, and be resistant to sweat. 3D-printed or injection-molded plastic may be inherently hard, rough, scratchy, etc. Techniques such as co-molding, multi-shot molding, silicone molding, and coating may be used to engineer the surface presented to the user.

The device may be placed loose inside an undergarment, or a user may prefer to clip or stick it to her body or a garment. A biocompatible adhesive, such as those used in adhesive bandages, may be uses in a disposable adhesive cover manner. However, such an adhesive may cause pain during removal and is typically not reusable. A light-tack, reusable adhesive may be preferred. A clip or other fastening device may also be used to attach the device to a garment.

Like the connector and electrical button, a discrete antenna component may not be preferred due to size and cost. Further, the performance of such an antenna, for example, with a Bluetooth radio, may be optimized for range, power consumption, and body absorption in a small device by designing the antenna into the electrical enclosure. Antenna traces may be realized by metal molding, co-molding, or transfer processes to integrate a very thin, custom antenna into the inside of the plastic enclosure.

The signal acquisition device may sample capacitance, resistance, voltage, a combination thereof, complex impedance, or other electrical parameters. Voltage measurement may be particularly useful for the detection of ammonia and/or methanethiol or (methyl mercaptan). An analog-to-digital converter (A/D or ADC) may be utilized with a corresponding full-scale acquisition value and resolution. To optimize the signal-to-noise ratio, it may be desired to maximize the ratio between the maximum sensor value and the full-scale range of the ND. Accordingly, it may be desired to minimize the added capacitance, resistance, impedance, etc. from the connector and case. Design techniques such as separating conductors, limiting trace lengths and overlaps, optimizing dielectric materials, high-resistivity materials, and shielding may be employed to reduce the parasitic contributions of the connector and case.

Flexible electronics may be utilized to make the sensor and signal acquisition device more user-friendly. A rigid circuit board and enclosure may be replaced with segmented components, allowing bending, hinging, or flexing along defined locations. Increasing levels of flexibility may be achieved by still placing small, rigid components (such as microchips and surface-mount passive devices) onto flexible circuit boards such as those comprising polyimide. Such flexible circuits will need flexible enclosures to translate the flexibility to the users. Rigid plastics may be replaced with increasing flexible plastics, possibly including rubber and/or silicone. A rigid enclosure may be replaced with a sprayed, dipped, or otherwise deposited coating. Such a coating may provide the required mechanical and electrical characteristics while being thinner and more flexible than a rigid enclosure.

Figure 18A:
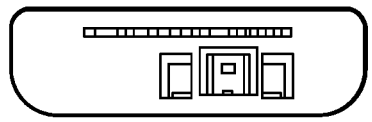
FIGS. 18A-18G are diagrammatic representations of case designs in accordance with the present invention.
Figure 18B:
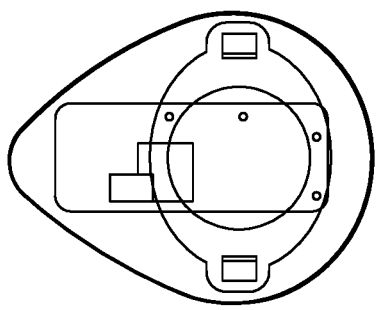
Figure 18C:
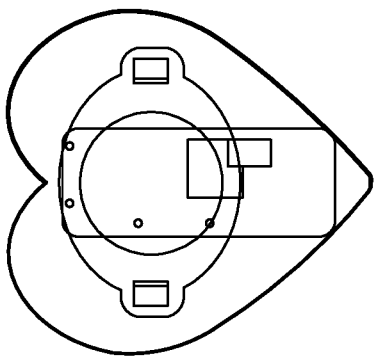
Figure 18D:
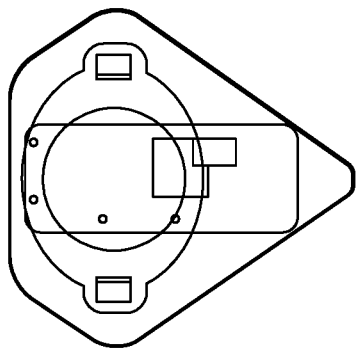
Figure 18E:
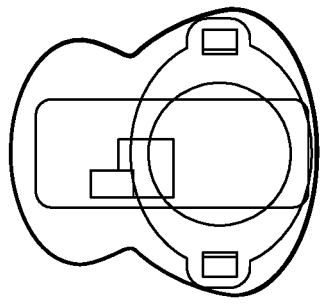
Figure 18F:
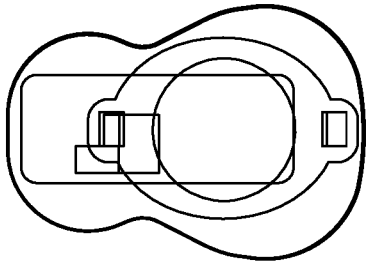
Figure 18G:
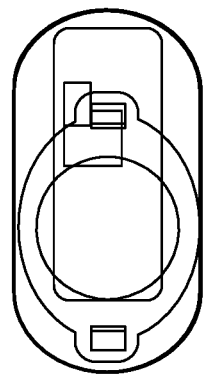

FIGS. 18A-18G illustrate several case designs for the signal acquisition device (exterior outlines with internal components superimposed) in consideration of size, comfort, and user preference. These various designs are exemplary in nature and are by no means an exhaustive representation of case designs. FIG. 18A shows a side view common to the top views shown in FIGS. 18B-18G. FIG. 18B illustrates a basic tear drop design, FIG. 18C illustrates a basic heart shape design, FIG. 18D illustrates a basic diamond shape design, FIG. 18E illustrates a first basic guitar design, FIG. 18F illustrates a second basic guitar design and FIG. 18 illustrates a basic pill design.

A personal hygiene product with a digital element can be, for example, in the form of a tampon, sanitary napkin, panty liner, and diaper, and the like. Specific examples have been described to illustrate embodiments of the device. These examples are for said illustration and are not intended to limit the scope of the claims in any manner. Accordingly, the description is intended to embrace all embodiments that may be apparent to those skilled in the art.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated but should be constructed to cohere with all modifications that may fall within the scope of the appended claims.

What is claimed is:

1. A personal hygiene product with a digital element comprising:
    a personal hygiene device to absorb menstrual fluid;
    a conductive sensor assembly disposed within the personal hygiene device, including one or more moisture sensors and at least one connector, said conductive sensor assembly generating a signal indicative of saturation level of said personal hygiene device when said conductive sensor assembly is in wetting contact with the menstrual fluid;
    an external digital element coupled to said conductive sensor assembly via the at least one connector, the external digital element including a substrate having a communication circuit capable of wireless communication with a smart hand-held electronic device, a processor, a power source, a first mating connector configured to couple to the at least one connector and optimized to be used with said conductive sensor assembly and a water-resistant case configured to house the components of the external digital element; and
    a signal transmission conduit comprising leads extending from said conductive sensor assembly and interconnecting said conductive sensor assembly to said external digital element via said leads, each lead having a termination that is in direct contact with the first mating connector.

2. The personal hygiene product with a digital element according to claim 1, wherein the personal hygiene device comprises a tampon.

3. The personal hygiene product with a digital element according to claim 1, wherein the personal hygiene device comprises a sanitary napkin.

4. The personal hygiene product with a digital element according to claim 1, wherein the personal hygiene device comprises a panty liner.

5. The personal hygiene product with a digital element according to claim 1, wherein the personal hygiene device comprises a diaper.

6. The personal hygiene product with a digital element according to claim 1, wherein the smart hand-held electronic device comprises a hand-held personal electronic device configured to interface with a user.

7. The personal hygiene product with a digital element according to claim 1, wherein the water-resistant case is configured to be mounted to an undergarment of a user.

8. The personal hygiene product with a digital element according to claim 1, wherein the water-resistant case is configured to be mounted to an outer garment of a user.

9. The personal hygiene product with a digital element according to claim 1, wherein the water-resistant case is configured to be attached to the body of a user.

10. The personal hygiene product with a digital element according to claim 1, wherein the first mating connector comprises a textured surface for the signal transmission conduit.

11. The personal hygiene product with a digital element according to claim 1, wherein the first mating connector comprises an interlocking mechanism for the signal transmission conduit.

12. The personal hygiene product with a digital element according to claim 1, wherein the first mating connector comprises a piercing connector for the signal transmission conduit.

13. The personal hygiene product with a digital element according to claim 1, wherein the signal transmission conduit comprises conductive thread.

14. The personal hygiene product with a digital element according to claim 1, wherein the signal transmission conduit comprises conductive thread woven into non-conductive thread.

15. The personal hygiene product with a digital element according to claim 1, further comprising a connector extension.

16. The personal hygiene product with a digital element according to claim 1, wherein the external digital element is reusable.

* * * * *